United States Patent [19]

De et al.

[11] Patent Number: 5,146,086

[45] Date of Patent: Sep. 8, 1992

[54] METHOD AND APPARATUS FOR IMAGING POROUS MEDIA AND METHOD FOR FABRICATING NOVEL OPTICAL MATERIALS

[75] Inventors: Bibhas R. De, Laguna Beach; Michael A. Nelson, Glen Avon; Kiran K. Pande, Laguna Hills, all of Calif.

[73] Assignee: Chevron Research and Technology Company, San Francisco, Calif.

[21] Appl. No.: 672,194

[22] Filed: Mar. 19, 1991

[51] Int. Cl.$^5$ ............................................. G01N 21/35
[52] U.S. Cl. ...................................... 250/253; 250/256
[58] Field of Search ...................... 250/253, 255, 256; 73/38

[56] References Cited

U.S. PATENT DOCUMENTS

| | | | |
|---|---|---|---|
| 4,782,501 | 11/1988 | Dixon et al. | 250/253 |
| 4,839,516 | 6/1989 | Freeman et al. | 290/253 |
| 4,994,671 | 2/1991 | Safinya et al. | 250/253 |
| 4,996,421 | 2/1991 | Rai et al. | 250/253 |

OTHER PUBLICATIONS

"Recommended Practice for Core-Analysis Procedure", American Petroleum Institute, API RP 40, First Edition, Aug. 1960, Section 3.4 and 3.5 pp. 18-36.
Research Methods Papers, Journal of Sedimentary Petrology, vol. 59, No. 4, Jul. 1989, pp. 613-635.
"Application of Capillary Pressure Measurements to the Determination of Connate Water Saturation", N. R. Morrow and J. C. Melrose, Interfacial Phenomena in Petroleum Recovery, pp. 257-669.
L. C. Uren, "Petroleum Production Engineering", Fourth Edition, pp. 660-669.
B. F. Swanson, "A Simple Correlation Between Permeabilities and Mercury Capillary Pressures", Journal of Petroleum Technolgy, pp. 2498-2504.

*Primary Examiner*—Janice A. Howell
*Assistant Examiner*—Richard Hanig
*Attorney, Agent, or Firm*—Edward J. Keeling; David J. Power

[57] ABSTRACT

A method and apparatus is described for determining petrophysical properties of porous media by the use of light transmission through the media. Specifically, by using a highly collimated light source, preferably a laser, the permeability, grain size, wettability, porosity and clay swelling behavior of a sample can be determined on the scale of millimeters. A calibration curve or function is first established to correlate light transmission through a slab of sandstone on the order of 5 to 10 mm under known conditions. This curved is then used to determine unknown conditions by measuring light transmission and comparing the values to those on the curve. Other applications for the phenomenon of light transmission through porous media are disclosed whereby conditions in a flowing stream of liquid can be monitored by use of light transmission. Specifically, changes in the refractive index and immiscible contamination can be detected. Finally, the phenomenon described can be used to model subterranean hydrocarbon bearing reservoirs, particularly fluid flow at different points in the reservoir, using light rather than hydraulic flows to simulate fluid flow patterns.

19 Claims, 13 Drawing Sheets

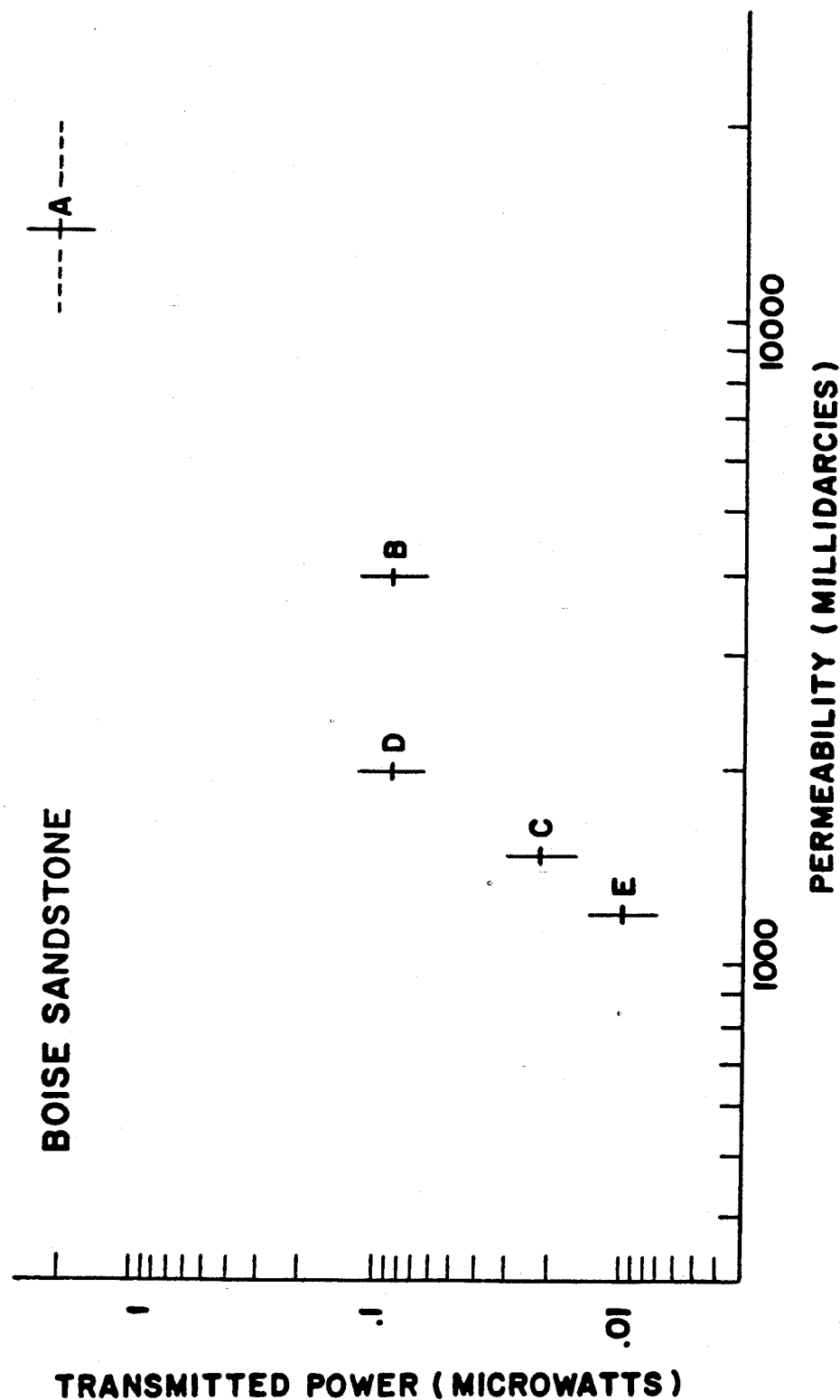

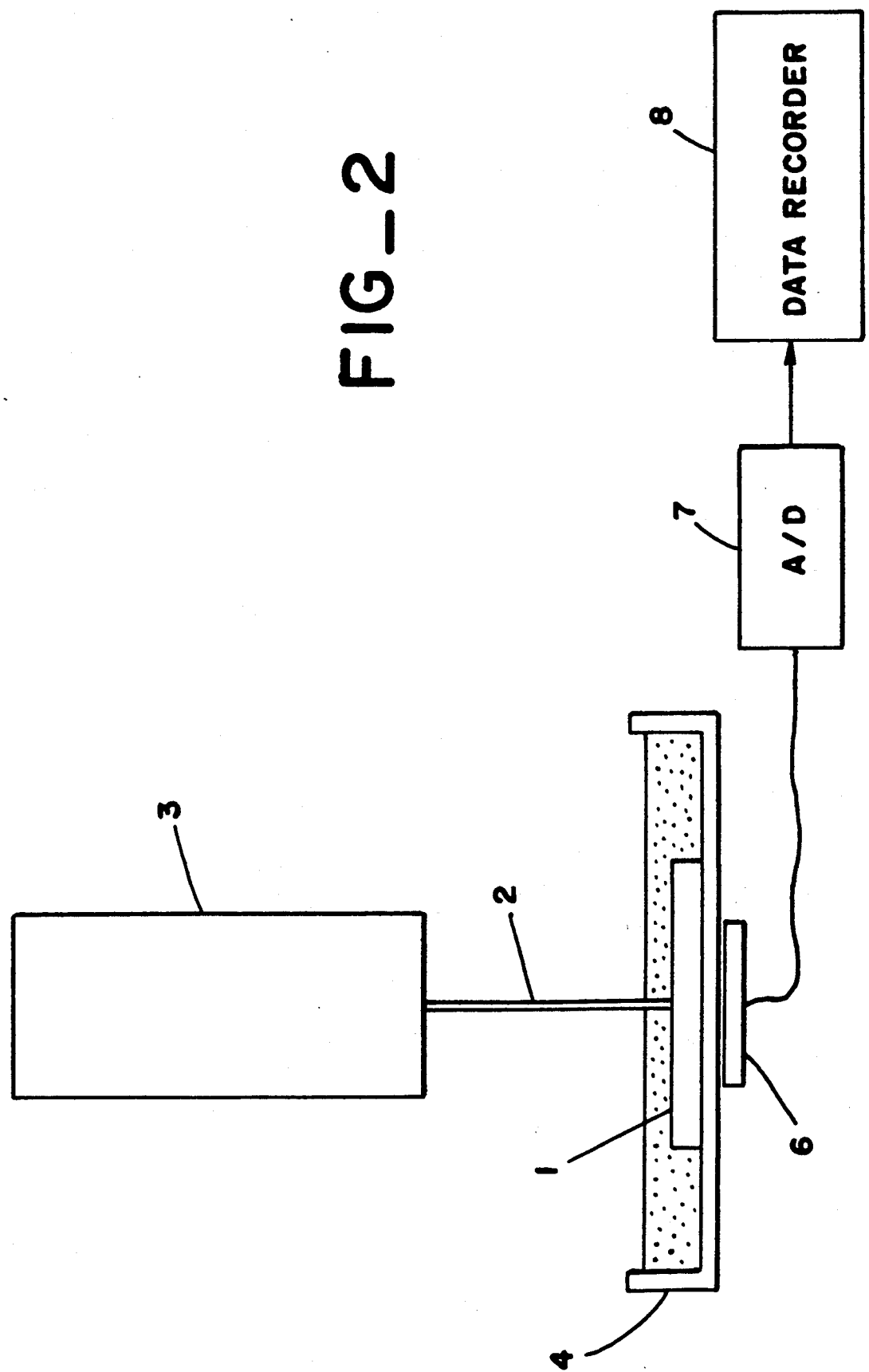

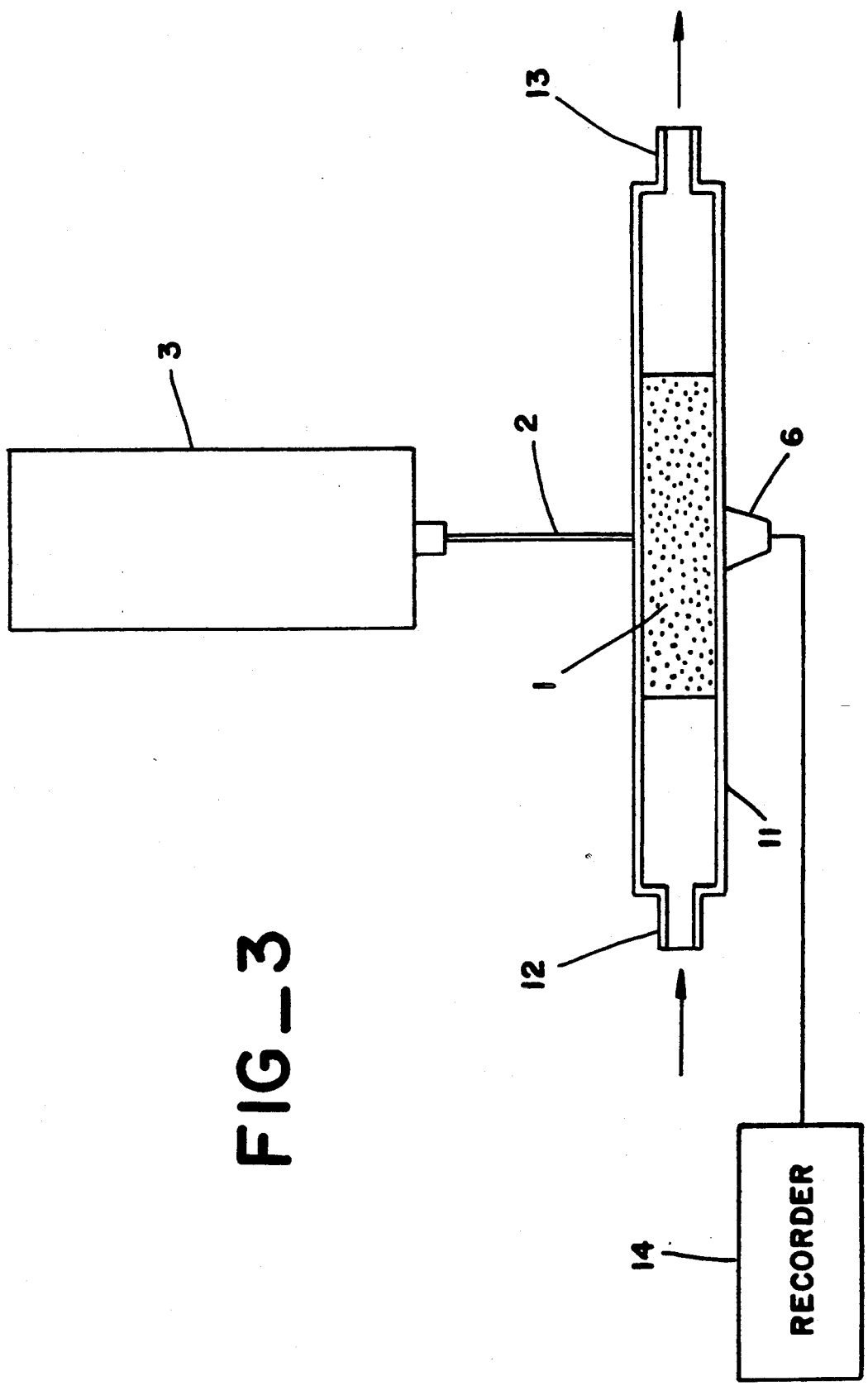
FIG_3

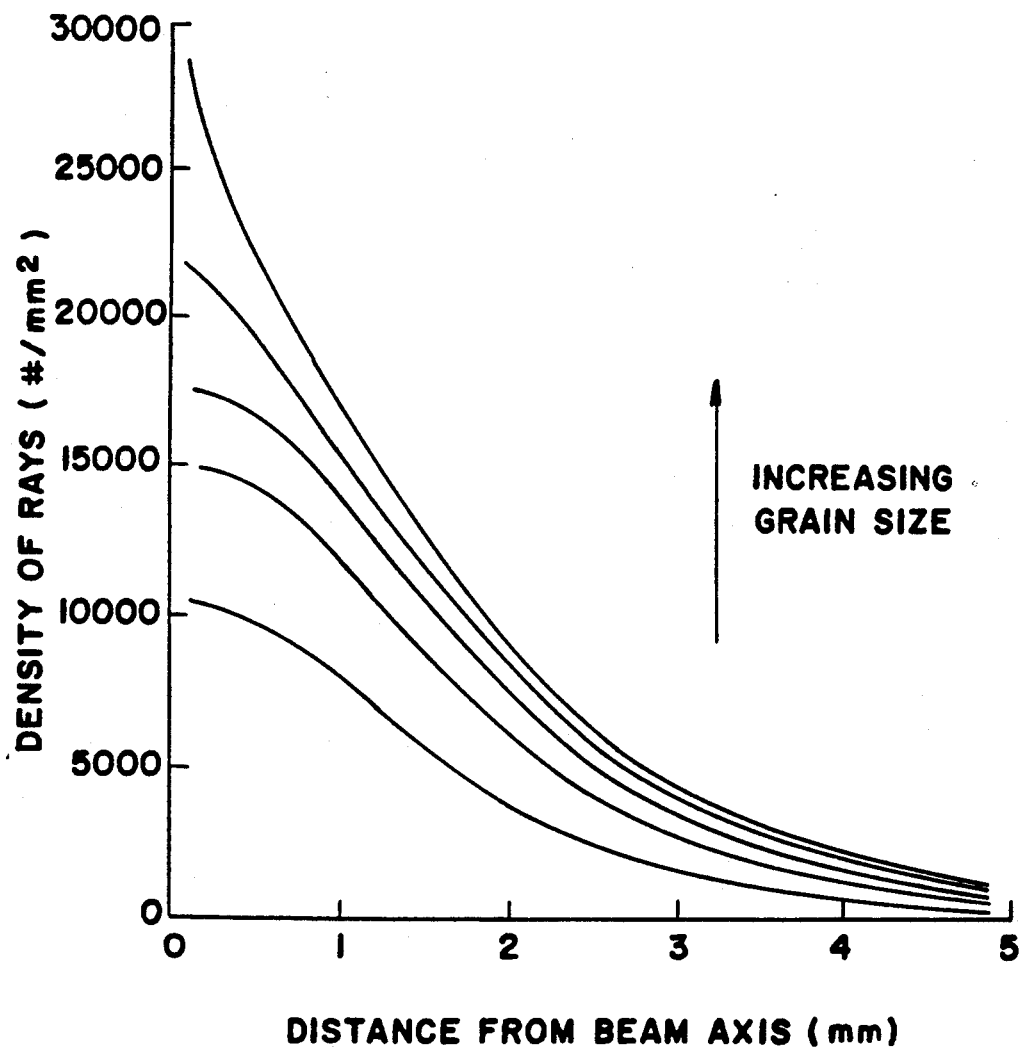
FIG_4

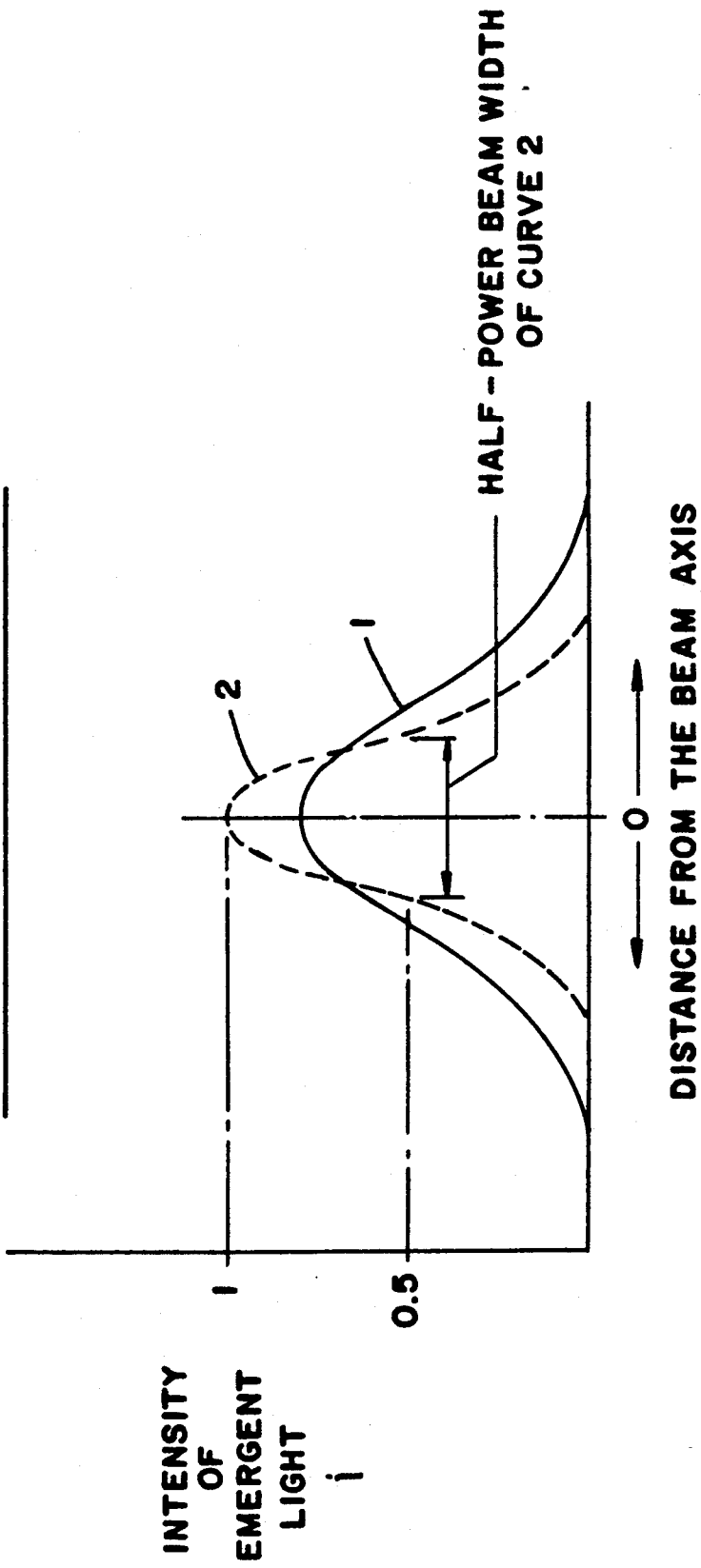
FIG_5

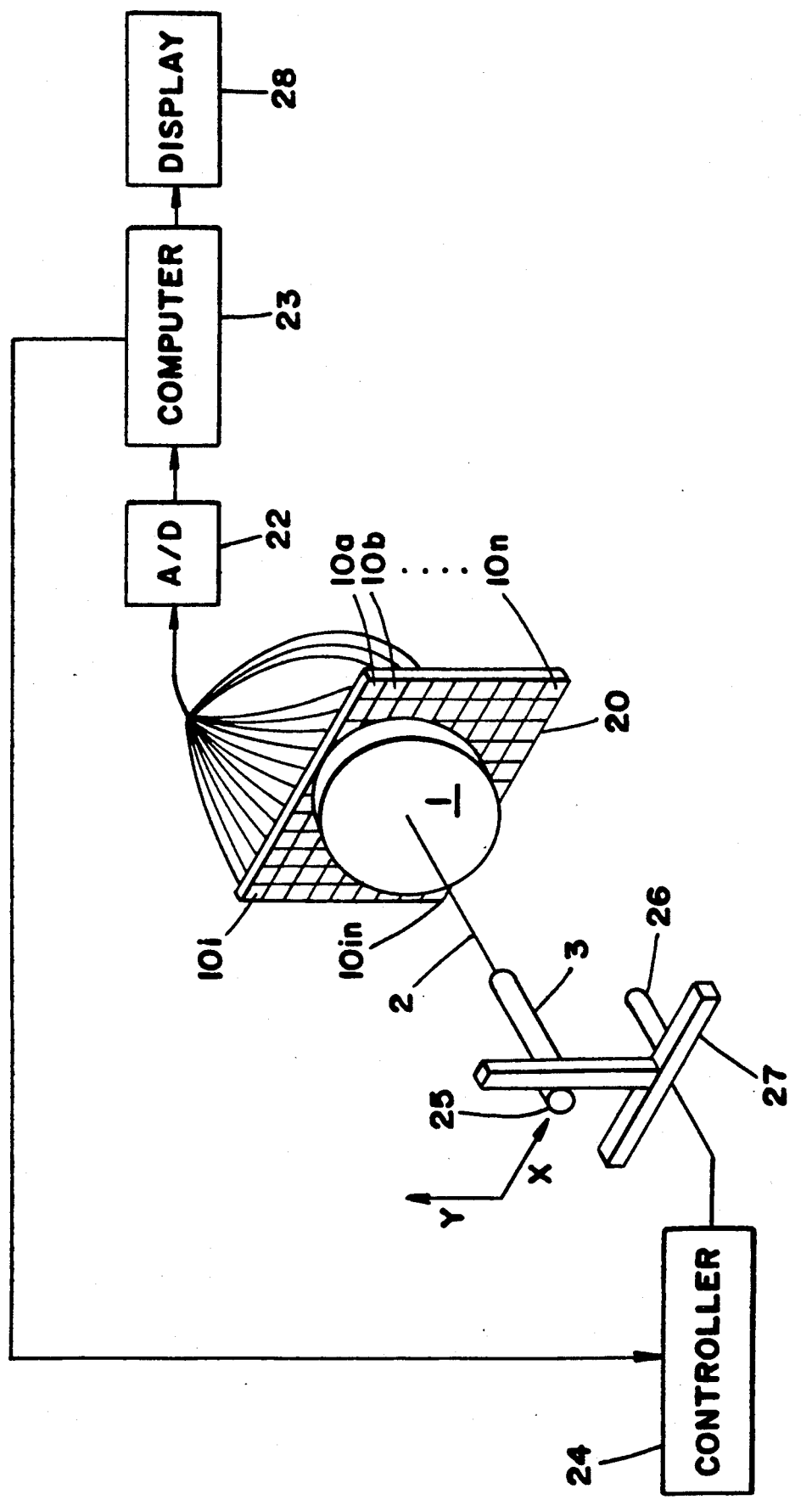
FIG_6

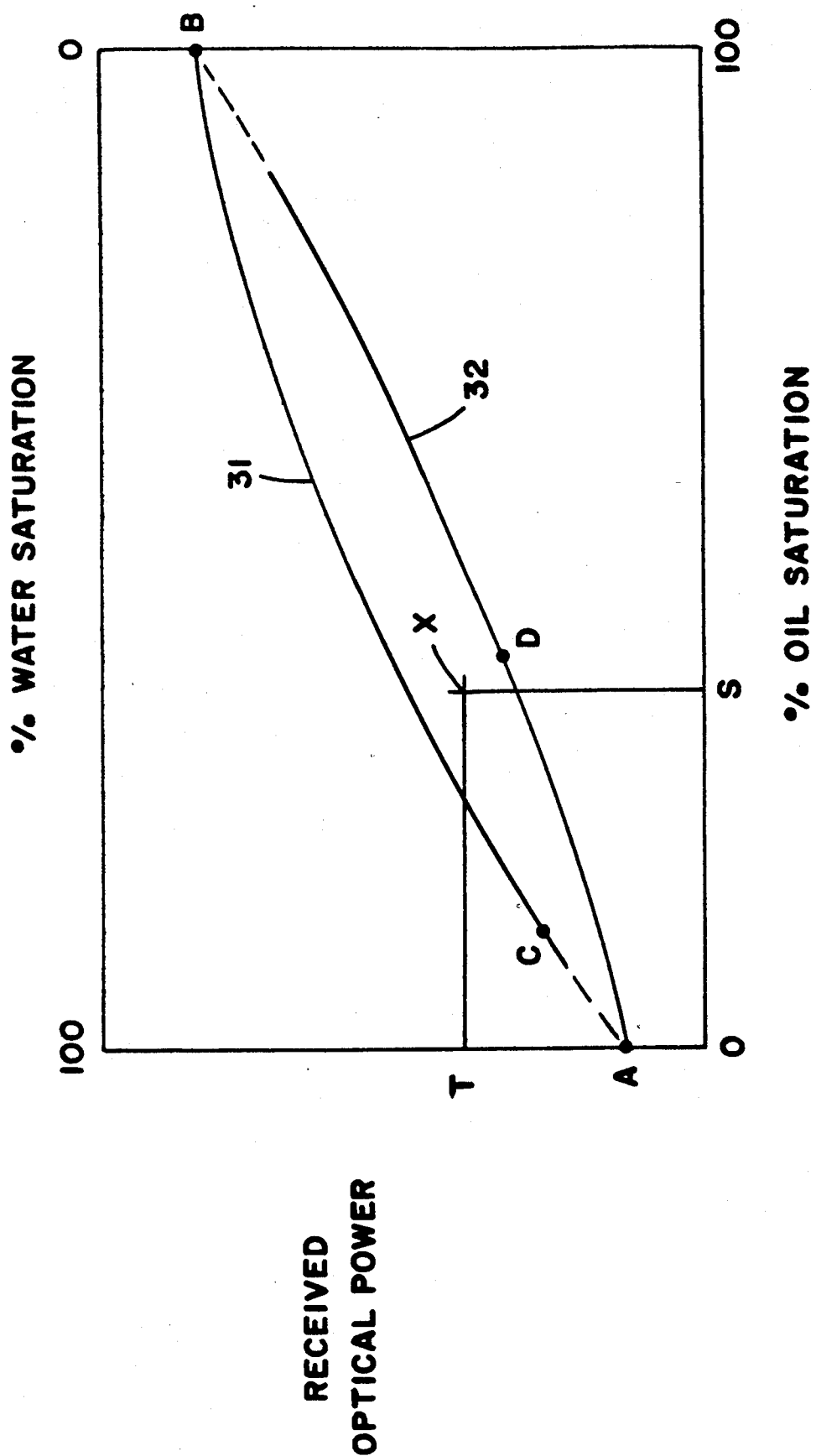
FIG_7

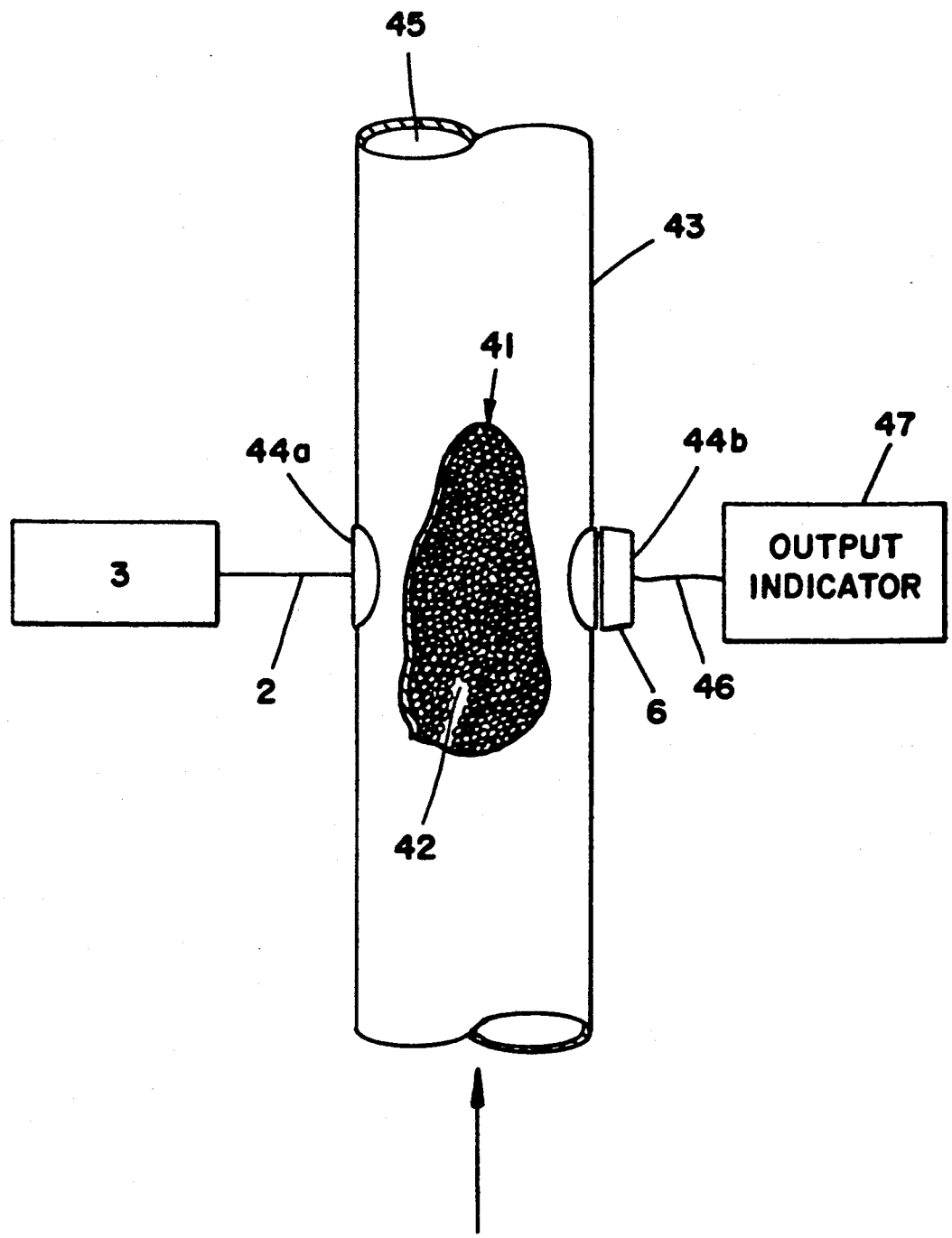
FIG_8

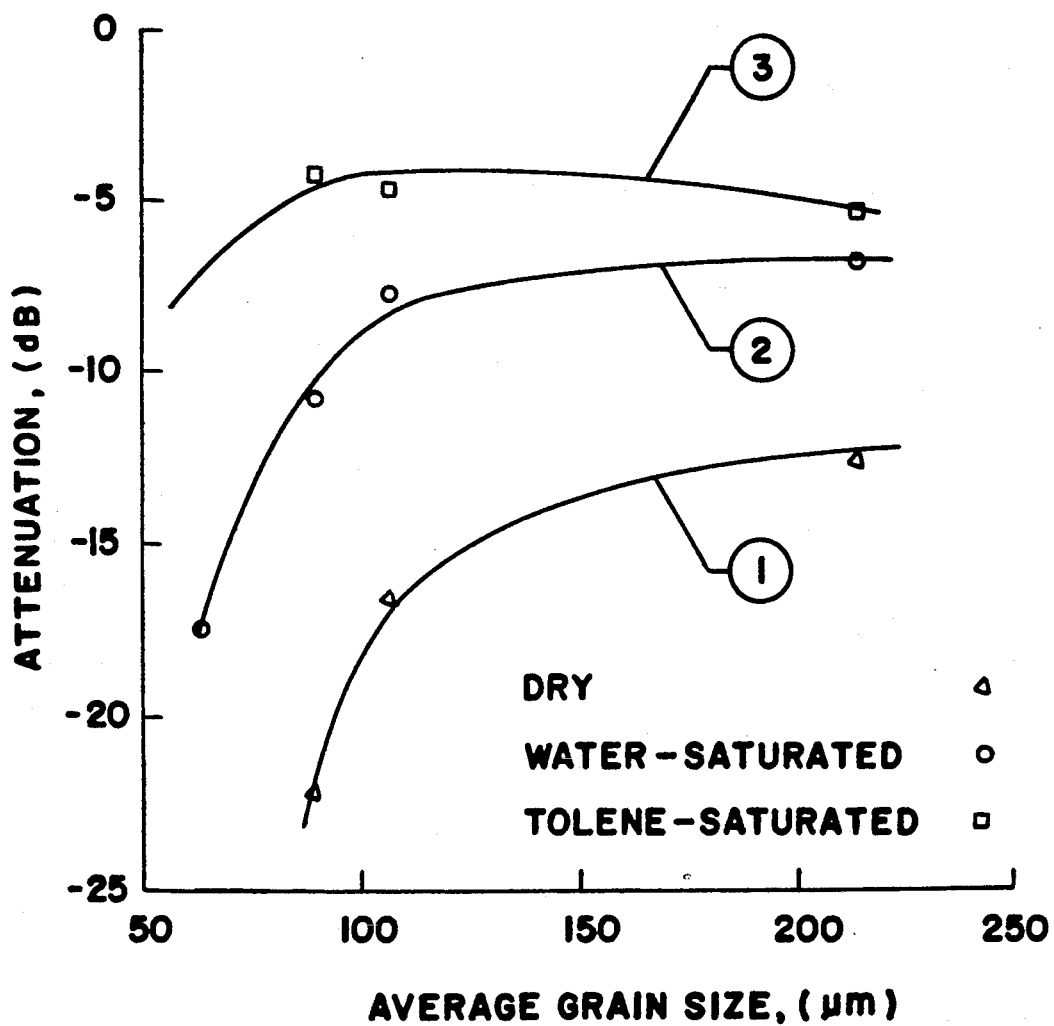
FIG_9

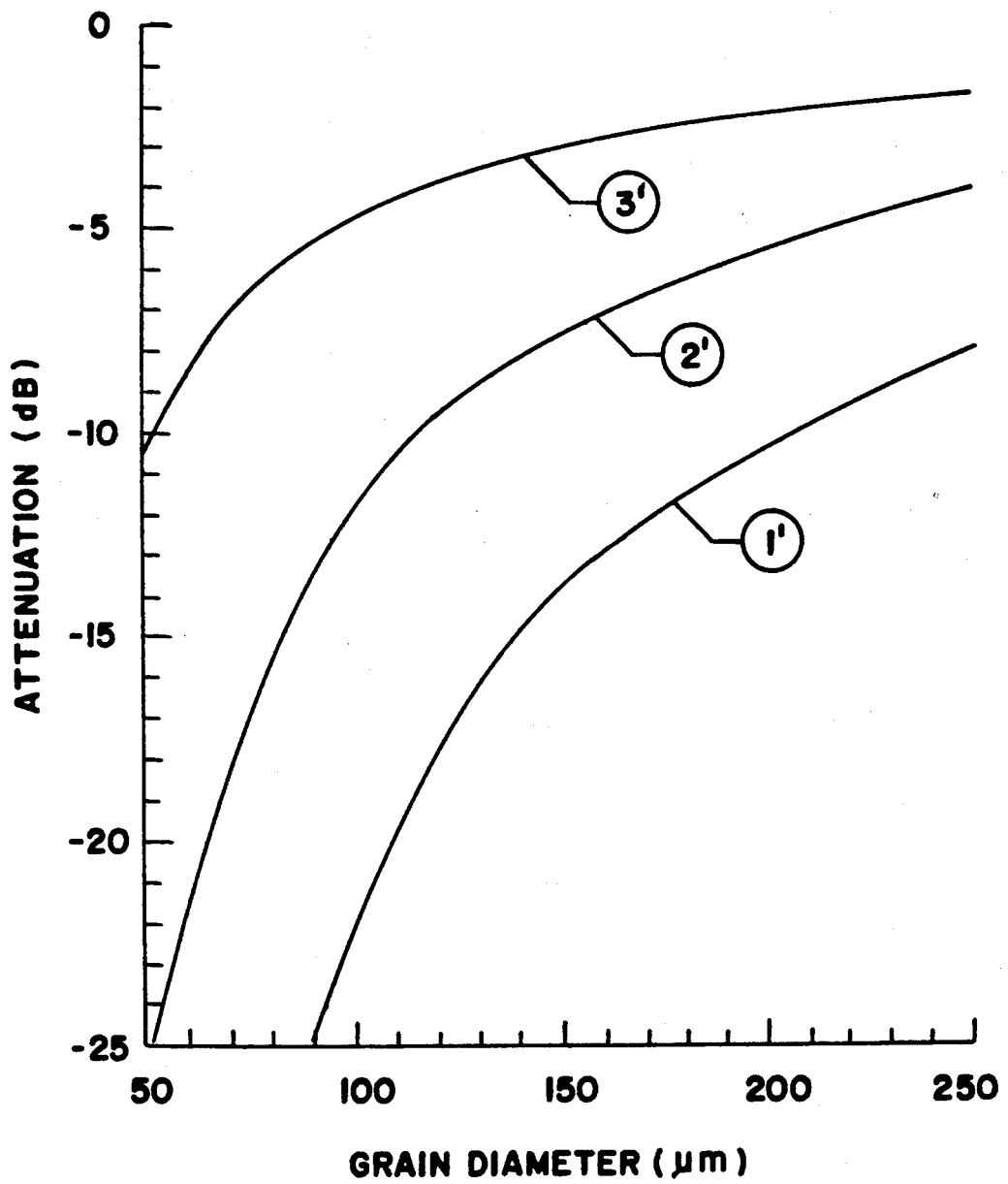
FIG_10

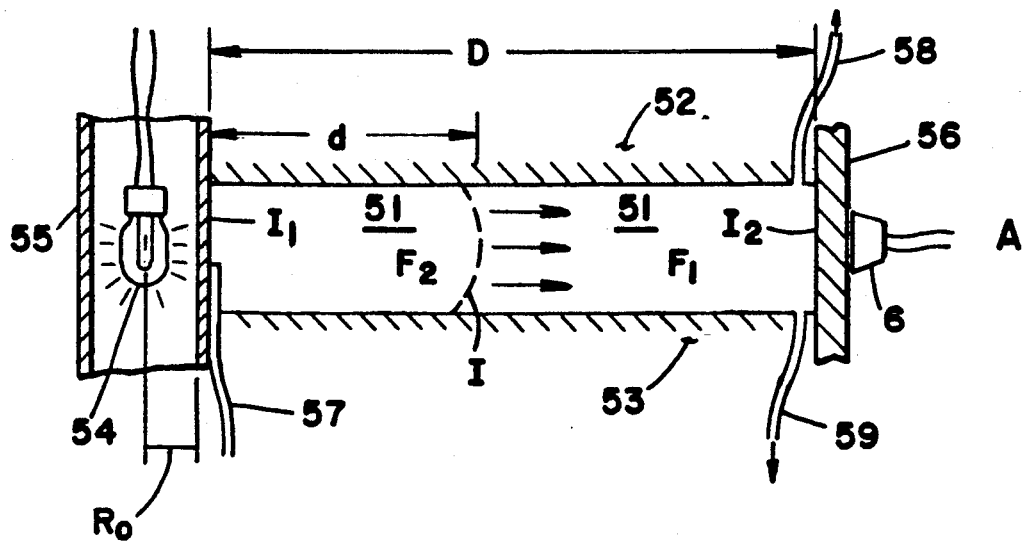
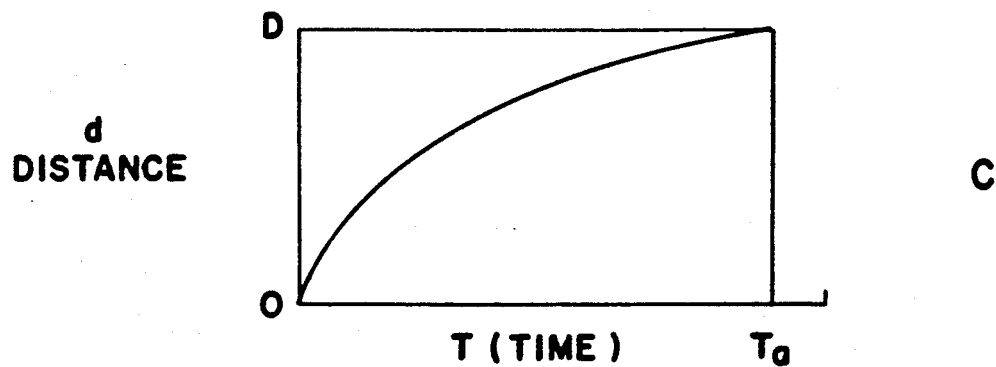
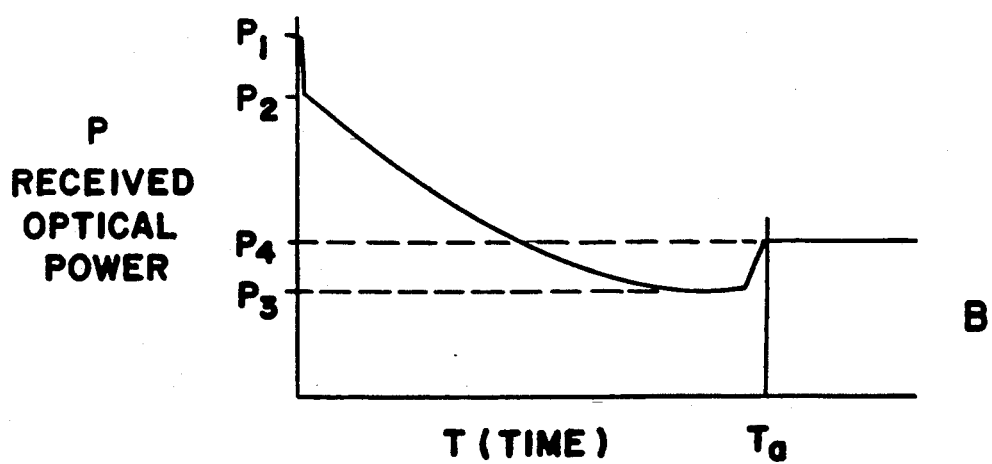
FIG_11

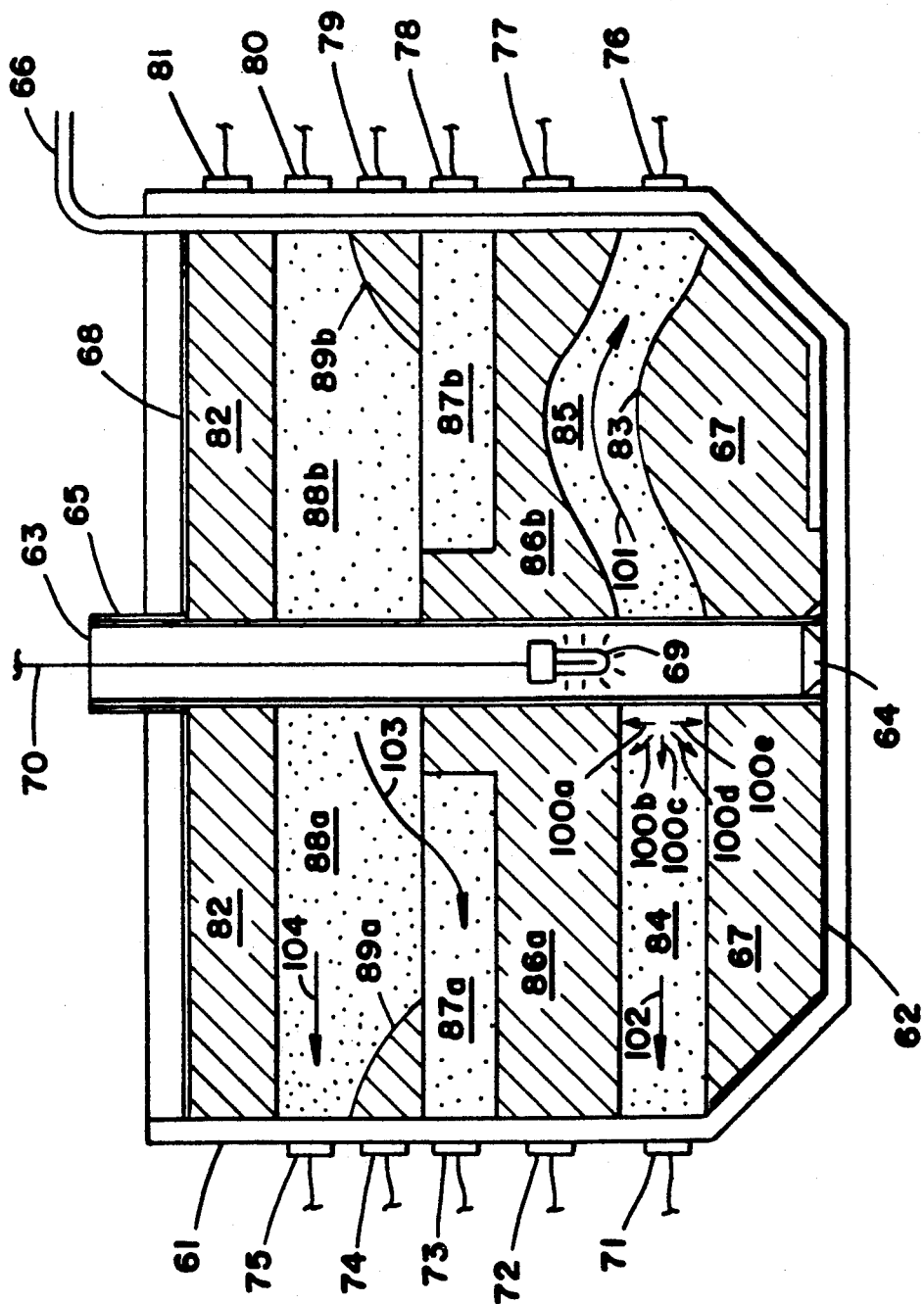
FIG_12

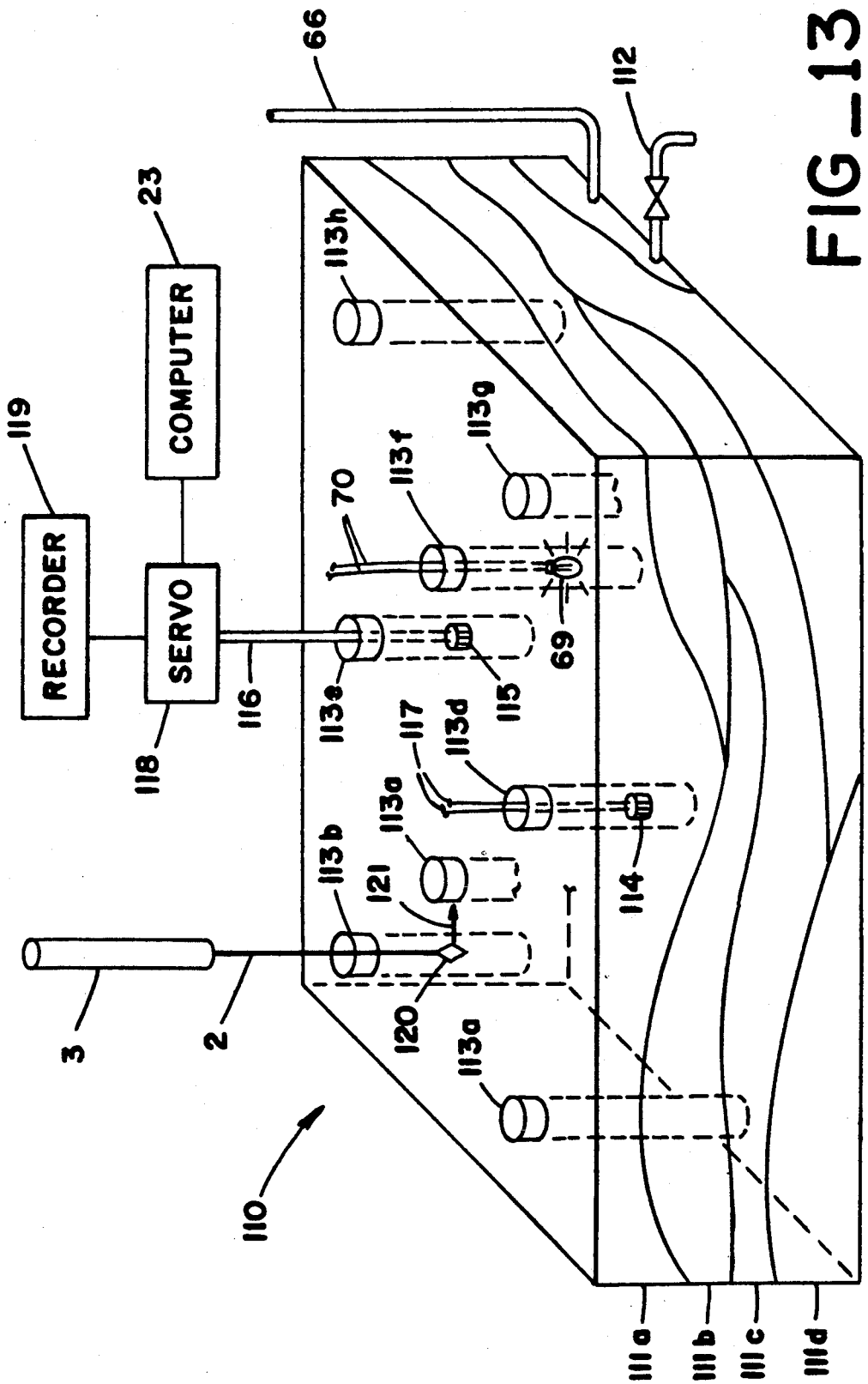
FIG_13

METHOD AND APPARATUS FOR IMAGING POROUS MEDIA AND METHOD FOR FABRICATING NOVEL OPTICAL MATERIALS

FIELD OF INVENTION

The present invention relates to the field of laboratory petrophysics, and more specifically, to using light to measure rock and fluid properties within a given formation.

BACKGROUND OF THE INVENTION

Determining subterranean reservoir properties is an important function for a wide array of applications, such as the production of minerals, e.g., oil and gas, groundwater technology and modeling contaminant transport in the subsurface. These properties include the permeability, wettability, porosity and grain size of the rocks, as well as the large scale flow patterns in the rock formations. The present invention lends itself to all of these areas.

The permeability of a material is a measure of the ability of a porous medium to transmit fluids through its pore spaces. For sufficiently slow, linear, incompressible steady flow it is described by Darcy's law:

$$K = \frac{q \mu L}{\Delta P A}$$

where
- K=permeability, darcys (d),
- q=flow rate, cc/sec,
- $\mu$=fluid viscosity, centipoise (cp),
- L=sample length, cm,
- $\Delta P$=fluid pressure differential across the sample, atmospheres (atm),
- A=sample cross-sectional area perpendicular to flow direction, cm$^2$.

The most commonly used permeability units are the "darcy" (d) and "millidarcy" (md). A rock having one darcy permeability conducts 1 cc/sec volume of 1 cp viscosity fluid through a cubic sample having 1 cm length sides under a pressure differential across the sample of 1 atm. Normally, permeability is determined by taking core samples from the reservoir and carrying out well defined measurement techniques, well known to those skilled in the art, on the samples. Several such techniques available for making these measurements are described in PETROLEUM PRODUCTION ENGINEERING - DEVELOPMENT by L. C. Uren, Fourth Edition, McGraw-Hill Book Company, Inc., 1956 and in American Petroleum Institute, API RECOMMENDED PRACTICE FOR CORE-ANALYSIS PROCEDURE, API RP 40, 1960.

More particularly, permeability plays a very important role in describing the fluid flow in oil and gas reservoirs. Two primary methods of measurement are practiced in the industry: steady state method and the dynamic displacement method. In each a cylindrical core is first saturated with water or brine and then oil flooded to irreducible water saturation. The core is then water flooded or brine flooded and the pressure drop across the core is measured along with the oil or water or brine production. The average saturations within the core are determined from the overall material balance. However, the steady state method requires lengthy measurement times since it requires stabilization of the fluid flow; while the dynamic displacement method does overcome this, it suffers from capillary end effects, and is therefore only effective for high flow rates.

Both of the above described methods of measuring permeability are additionally limited in the information they provide. Specifically, both methods provide only the average or bulk permeability for the core, and can only achieve a resolution on the order of about an inch or so, where core diameters are in the range of 1 inch to 4 inches. Additionally, it is well known that permeability can vary considerably in sandstones over a distance of only one or two millimeters. The degree of variation in permeability has justifiably received much attention in recent years. Information about permeability variation within a formation can provide valuable information about the geological characteristics of the formation. This information is useful in predicting how an oil field will develop, the yields that can be expected, and how it might compare or contrast with already known and developed fields. Running flooding permeability tests, as described above, on very small diameter cores is not an acceptable solution to the problem, since the permeability can still vary considerably along the length of the core. Furthermore, running flooding tests on small diameter, small length cores is not practical because of hydraulic sealing problems and problems introduced by boundary effects.

The only known method that employs light transmission for estimating permeability is by examination of thin sections of the core. Thin sections of geologic samples less than 60 $\mu$m thick are customarily examined with petrographic image analysis techniques to study the micro-features of the sample. From this analysis, geological interpretations of the depositional and post depositional process which formed the sample can be derived. Moreover, physical qualities such as the porosity and permeability of the sample can be estimated. The permeability of the sample, which depends on an interconnected network of individual pores, can be estimated from the porosity of the sample by a linear regression formula or by the empirical Kozeny-Carman equation. Since a thin section has no meaningful permeability itself, the above method gives only an indirect and qualitative estimate of the permeability of the parent volume of rock from which the sample was derived.

A need thus exists for a method to directly measure the permeability and permeability variation in a core having a macroscopic thickness (i.e. a thickness of many layers of grains), with resolution on the order of millimeters. There have been some efforts to obtain permeability measurements in the "less-than-bulk, greater-than-microscopic" range, but most proposed methods are time consuming and cumbersome. For example, Chandler, et al. in their article, "A Mechanical Field Permeameter for Making Rapid, Non-Destructive Permeability Measurements," J. Sedimentary Petrology, 59, 613 (1989), discuss an apparatus (an "air minipermeameter") which achieves a resolution on the order of 2 cms. While this is an improvement over the bulk method, it can still overlook important variations on the millimeter level. Swanson, in his article "A Simple Correlation Between Permeabilities and Mercury Capillary Pressures," J. Petroleum Tech., 33, 2498 (1981), discusses a method for determining the permeability of tiny chips of rocks using mercury injection porosimetry. While this method may provide the desired resolution, it is cumbersome and does not provide for a continuous plot or "map" of the permeability and its variation across the core.

The problem of wettability, of great interest in petroleum production problems, concerns knowing when two fluids (e.g., oil and water) and present in the rock pore space, which fluid adheres to, or "wets", the pore walls or the surface of the rock grains, while the non-wetting fluid occupies the voids between the grains or the pores. The importance and application of this problem is discussed in "Application of Capillary Pressure Measurements to the Determination of Connate Water Saturation," by N. R. Morrow and by J. C. Melrose in *Interfacial Phenomena in Petroleum Recovery* (N. R. Morrow, ed., Marcel Dekker, N.Y., 1991). At present there exists no non-invasive, non-destructive method by which one can determine whether oil or water wets the surface of the rock grains when both fluids are present.

While the permeability of a rock contains information about the grain size, in petrophysical studies it is of fundamental importance to make measurements of the grain size itself. This parameter can be determined from either microscopic measurements, or by measuring with sieves of known grid sizes upon disaggregating the rock into the constituent grains. Alternately, apparatus are commercially available which can determine the grain size of a rock sample by use of a laser. One such apparatus is sold under the name MICROTRACR ® by Leeds & Northrup Co. Operation of this apparatus is described in detail in "Rapid Analysis of Submicron Particles," by P. E. Plantz and H. N. Frock. This apparatus requires a sample of the composite medium to be disaggregated, the particles are then blown in a cloud through a laser beam, with the resulting scattering effect of the laser being correlatable to the particle size. This effect is also discussed in "Measurement of size and concentration of scattering particles by speckle photography" by Genceli, et al., J. Opt. Soc. Am., V70, 10, 1212, wherein the authors admit, "there are moderate restrictions on the number of particles per unit volume."

The permeability of rocks may be affected by the reaction of clays within the rock. Typically, in their natural state within a subterranean formation, clays are compacted around the grains of the rock. Once the natural source fluid is replaced with another fluid, the clays may swell, plugging the channels connecting the pores, and lowering permeability. It is desirable to know not only the total change in permeability, but also the rate at which permeability changes. Current means in the art for determining the effect that different fluids may have on permeability require flooding the core with the various fluids and measuring the bulk permeability. In this manner, however, data can only be collected at various times, rather than in a continuum. Furthermore, it is difficult to determine, with this method, precisely how the permeability may be changing as a function of time.

Previous methods of optically characterizing cores have concentrated on reflected light. Herbin, et al. disclose In U.S. Pat. No. 4,852,182 a method of longitudinally splitting a core and imaging the cross section by reflected normal light. Along a similar vein, Pruett, et al. in U.S. Pat. No. 4,616,134 disclose a method and apparatus for optical surface scanning of longitudinal cores. However, neither of these methods actually measures properties of the core, other than its variation in color.

Recent advances in imaging technology have been applied to the area of geologic samples. For example, Smith in U.S. Pat. No. 4,797,906 teaches a method to measure porosity in thin sections by use of X-ray reflectance to stimulate naturally occurring fluorescence in the sample. NMR (Nuclear Magnetic Resonance) has been used in U.S. Pat. No. 4,728,892 wherein Vinegar, et al. teach a method for determining, among other petrophysical properties, permeability by indirect calculation from measured porosity. Vinegar et al. state that a high resolution (1 mm) can be obtained with NMR imaging, however, the method is limited to cores 4.2 cm or less in diameter. In U.S. Pat. No. 4,868,751 Dogru, et al. claim a method for determining permeability that combines the classic method of confining the core to a pressure sleeve with the technology of CAT (Computer Aided Tomography) scanning during the flooding. Dogru, et al's method purportedly eliminates capillary effects on permeability in the core, but does not indicate that the method gives a high resolution image of the variation in permeability within the core. None of the methods either teach or suggest the use of light transmission through the sample to measure permeability.

The porous media that are the focus of this invention are non-absorptive to light. A good example of an absorptive material is a thin film of black plastic; while the medium is very thin, no light passes because it is absorbed by the medium. In non-absorptive materials, light might be expected to transmit through the medium and emit from the other side, which it does in many cases. However, in some instances some or all of the light which is transmitted into the non-absorptive medium may not be transmitted through the medium due to diffusion of the light inside the medium. A good example of this latter category is a dense pack of irregular quartz crystals not unlike sandstone.

Light transmission through composite media is a subject that has received much attention recently. Current theories and studies of the phenomenon concentrate on the scattering of laser light within the medium in order to study the mechanism of propagation. Typically, the medium is a smoke or vapor or particles suspended in a fluid, gel or solid with particle densities so low that normally occurring light can easily pass through. (e.g., Ishimaru, Kuga, et al., "Scattering and Diffusion of a Beam Wave in Randomly Distributed Scatters," J. Opt. Soc. Am. 73, 131–136, 1983). Other studies have considered the phenomenon of light transmission through a porous bed of spherical glass, as for example Gate, "The Determination of Light Absorption in Diffusing Materials by a Photon Diffusion Model", J. Phys. D.: Appl. Phys., 4, 1049–1056, 1971 (Great Britain). In these studies, the porous media have been transparent to visible light, and so the propagation of laser light through them is not surprising. The concept of laser light transmission through media normally opaque to light was considered and discussed in a paper by Anderson, "The Question of Classical Localization—A Theory of White Paint?", Philosophical Magazine B, 52, 3, 505–509, 1985. In his paper Anderson theorized a slab of thickness W of material containing random non-absorptive scatters embedded between two non-random propagating media. Stating that if the slab is thick compared with the conventionally defined mean-free-path 1, coherent radiation will be exponentially attenuated, Anderson went on to state that most of the incident radiation will be scattered diffusely and, since it has been postulated that there is no absorption, the radiation must all come out on one side or the other of the slab W. Thus there is a clear distinction between the transmission of diffuse, incoherent radiation of a "localized" system and an "extended" system, once the system is sufficiently large. Unfortunately, "sufficiently large" also means "sufficiently opaque" and the experimental problem may not be all that simple according to Anderson, therefore optimum scattering requires structures comparable to the wavelength (i.e., particle diameter is approximately equal to wavelength). In addition, although great complexity may be encountered, the work may impinge on a number of highly interesting and practical systems, such as porous media. This therefore indicates that light transmission through a non-absorptive porous medium such as a macroslab of sandstone, as described herein, is not to be expected at all, since in sandstone the wavelength of a laser light is much less than the particle diameter, and the macroslab, due to its thickness, is sufficiently opaque.

Others have additionally theorized about light transmission in rock. In a paper titled, "Reflectance and Albedo Differences Between Wet and Dry Surfaces", Twomey, et al., Applied Optics, 25, 3, 431–437, 1986, the authors discuss why light is preferably absorbed by wet rock over dry rock. The theories developed in this paper suggest that forward light scattering into porous media is dependent on the type of fluid present in the voids. However, the focus of the article is absorption by the media rather than transmission by the media, and no speculation is made as to light continuing to propagate through the media, or that the amount of light transmitted into (i.e., absorbed by) the media might be correlated to the overall permeability of the media.

In petroleum production problems and groundwater studies, it is necessary to predict fluid flow characteristics in a stratified earth, where the permeabilities of the various strata are known or given. Such characteristics are usually determined from computer simulations. In conjunction with such simulations, it is useful to have a scale-model laboratory "reservoir" where the predictions of the simulation can be verified. Thus, what is needed in the art is a simple, non-destructive, non-invasive, effective method for determining various properties of a porous medium. Such properties include permeability, grain size, wettability, porosity and clay swelling of a porous medium, as well as the absence or presence of fluid in the porous medium, type of fluid present, and scale modelling of fluid flow patterns in a stratified porous medium. We have recently discovered that laser light will be transmitted through a macroslab of sandstone, on the order of 1 mm to 20 mm thick, preferably 5–10 mm thick. A phenomenon not expected since such a slab is ordinarily opaque to visible light. We have further determined that the amount of light transmitted through the macroslabs is correlated to the permeability of the slab at the point of transmission. Additionally, we have discovered that the laser transmission through a consolidated sandstone allows for determination of average grain size where the sandstone has a high concentration of particles per unit volume; thereby allowing a nondestructive measurement of said grain size. We have still further discovered that the transmission of the laser light through a macroslab containing water and white oil is dependent upon which of the two fluids wets the grain surface, and allows for a method for continuously monitoring the change in permeability with respect to time in a macroslab core section flooded with various fluids. Finally, it has been found that use of the transmission phenomenon allows for prediction of fluid flow characteristics when used in conjunction with computer simulation, wherein scale model reservoirs are constructed so that light transmission in said models can be observed and measured.

SUMMARY OF THE INVENTION

The claimed invention provides a method and apparatus for imaging properties of porous media by light transmission through the media. The invention takes advantage of a recently discovered phenomenon that laser light will penetrate a macroscopically thick slab of porous material which is normally opaque to random visible light. Further, the amount of light transmitted through the medium is correlated to various properties of the medium and depends on the types of fluid present in the voids of the medium. Thus, by impinging an intense, preferably collimated light on one side of a porous medium and measuring the amount of light transmitted through the medium, one can determine the permeability, the grain size, the porosity, and the wettability of the medium; as well as the presence, quantities and distributions of certain fluids within the medium.

In one embodiment, the invention is used to measure the permeability of porous media as for example sandstones from geologic formations such as petroleum reservoirs. A conversion function relating light transmission to permeability of the rock for a given fluid is first established by control laboratory measurements and curve fitting. This function can be used for all samples from the same formation (i.e., the same rock type). A laser beam is then impinged on a core sample a few millimeters thick. The sample is scanned by the laser, and a sensor opposite the laser records the light transmitted through the core. The recorded data can then be converted to permeability by the conversion function, and be displayed graphically by any of several means known in the art to give a topological "map" of the permeability. In a variation on this embodiment, a core sample containing clays is flooded with various liquids; the effect the liquid has on the permeability due to clay swelling is measured by light transmission through the sample. In this way, the change in permeability as a function of time can be observed. This same time dependence of permeability can be observed where an initially undisturbed, saturated core section is subjected to dynamic flow. The flow will cause fine intergranual particles to migrate into the pore throats, blocking the flow.

In a second embodiment the invention is used to determine the mean grain diameter of porous media, including naturally occurring media such as sandstones. Reference curves are generated either from computer simulation or measurement of light diffusion in samples of known grain size. The experimental results are then compared to the reference curves to determine actual grain size.

In a third embodiment the invention is used to determine the wettability of porous media such as sandstones. A reference curve is first established correlating light transmission to percent oil and water for both water wet and oil wet conditions. A sample saturated with a known oil/water concentration can then be tested and the results compared to the reference curve to determine if the grains are oil wet or water wet or are in a state of mixed wettability. In a variation of this embodiment the heterogeneity of saturation in a partially desaturated slab of sandstone can be mapped.

In a fourth embodiment the invention is used to determine the presence or absence of a fluid in a porous medium. The fluid can either be static or flowing, and the porous medium can be either naturally occurring or artificially fabricated. Further, the presence of one of two fluids having distinct refractive indices can be determined, as well as detecting mixing of miscible and immiscible fluids with distinct refractive indices. The method is similar to that for measuring permeability, but the conversion function is established for light transmission versus type of liquid, rather than permeability.

In a fifth embodiment of the invention, porous media are used to fabricate scale models of petroleum reservoirs. A light source is then used to simulate fluid flow, and light detectors can be used to predict fluid flow patterns within the reservoir. The embodiment can generally be used to predict fluid flows in any porous medium.

The primary advantage of the claimed method over current methods is that the specific petrophysical property of interest can be measured at a high spatial resolution and further, that the measurement of permeability does not necessitate hydraulic flows in the sample requiring high pressure plumbing, seals, etc.

These and other objects, features and advantages of the present invention will become apparent from the following detailed description, wherein reference is made to the Figures in the accompanying drawings.

BRIEF DESCRIPTION OF THE DRAWINGS

In order to facilitate the understanding of this invention, reference will now be made to the appended drawings of the preferred embodiments of the present invention.

FIG. 1 is a plot of data showing the relationship between laser light transmission through a sandstone and permeability of the sandstone.

FIG. 2 is a drawing of an apparatus for measuring the transmission and attenuation of a laser light through a dense porous medium.

FIG. 3 is a drawing of an apparatus for measuring the change in permeability of a core sample.

FIG. 4 is a plot of simulated data predicting the intensity distribution of the emergent beam from dense porous media as a function of the distance from the axis of the impinging laser beam and the grain size of the media.

FIG. 5 is a sketch of the intensity of laser light transmitted through a slab of sandstone as a function of the distance from the axis of the laser beam.

FIG. 6 is a drawing of an apparatus for measuring the grain size of a porous medium with a laser.

FIG. 7 is a sketch showing the dependence of light transmission through a porous medium saturated with two fluids, on the fluid coating the grains of the medium.

FIG. 8 is a drawing of an apparatus for monitoring fluid passing through a porous medium.

FIG. 9 is a plot of experimental data showing the dependence of the attenuation of a laser through dense porous media on the grain size of the media and the index of refraction of the fluid saturating the media.

FIG. 10 is a plot of simulated data predicting the dependence of the attenuation of a laser through dense porous media on the grain size of the media and the index of refraction of the fluid saturating the media.

FIG. 11 is a drawing showing the relationship between light received by a detector in a model reservoir and the proximity of a moving fluid interface to the detector.

FIG. 12 is a drawing of a scale model of a geological reservoir using porous media and light to simulate fluid flow.

FIG. 13 is another drawing of a scale model of a geological reservoir using porous media and light to simulate fluid flow.

DETAILED DESCRIPTION OF THE PREFERRED EMBODIMENTS

The claimed invention makes use of a recent discovery by the inventors, combining two unrelated disciplines to develop the present invention. In the first discipline, petrophysics, it is known that the size of the grains in a porous medium will affect the permeability, i.e., in comparing two porous media, one with large grains, one with smaller grains, yet having identical porosity (i.e., void volume), the medium with the smaller grains will have a lower permeability. This is attributed to the higher surface area and consequent increased viscous drag on the flowing fluid. In the second discipline, optical physics, it is known that, when the wavelength of the source light is very small compared to the size of the particles of the porous medium, the diffusive attenuation, or lessening, of light through the medium is a function of the particle size.

This attenuation is due to the greater number of surfaces and the consequent increase in scattering events, and thus diffusion. However, as the theory of light propagation is generally applied to porous media made of glass spheres, and the forward propagation phenomenon, known as forward scattering, is usually explained in view of this geometry, it is not obvious to what extent this phenomenon would apply to sandstone; a medium comprising mineral quartz crystals having irregular shapes and sizes generally in the range 10–1000 $\mu$m. The grains in sandstone, for example, are transparent, sometimes having a milkiness or a color to them, and, in free form, are better known as common sand. As common sand is not observed to be transparent there is no reason to expect sandstone to be transparent, and in fact, it is not transparent to naturally occurring light and most artificial light. Even after we theorize that the attenuation of light transmission through sandstone should have a correlation to permeability, in that both are dependent on grain size, the known opaqueness of sandstone suggests that the phenomenon would not be observable, and therefore would not be of any practical value.

It is known from common experience that when grains of one transparent medium are surrounded by a fluid with an index of refraction approaching that of the medium, the medium tends to "disappear" due to the lack of refracted light. For example, glass beads in water are less "visible" than glass beads in air; the index of refraction of water being nearer the index of the glass beads than is the index of air. Therefore, one might speculate that since a "wet" medium is more light-conductive than a "dry" medium, that light might propagate better through wet sand than dry, and the phenomenon could be used to advantage. Yet practical knowledge that wet sand is not transparent in naturally occurring and most artificial lights teaches away from pursuing such a theory.

In experiments attempting to find some correlation between permeability of porous media and light transmission through porous media, we discovered that a sandstone or sand pack, normally opaque, will in fact transmit collimated light when the medium is saturated with a clear fluid having an index of refraction "n" greater than air and most gases (i.e., n=1.0), and further, that the amount of light transmitted through the medium is related to the permeability of the medium at that point, i.e., the higher the permeability, the greater the quantity of light that will be transmitted. However, the effect of attenuation of the light signal relative to the permeability decreases as the index of refraction of the saturating fluid approaches that of the medium itself; at that point where the two indices are equal, the medium becomes completely transparent and there is no attenuation of the signal in the medium. The attenuating effect will occur for saturating fluids with refractive indices greater than and less than the medium itself, but at some point if the difference between the two indices becomes too large, the attenuation increases to the point where little or no light is transmitted. Although some light transmission through dry sandstone has been observed and is even predictable in some instances, the present invention anticipates that the medium will be saturated with a liquid when lasers of relatively low power are used. For high power lasers, the invention will work without the presence of the saturating liquid.

The laser is preferably used as the light source because of its highly collimated nature, wherein coherent beam diameters of less than 1 mm are not uncommon, which maximize propagation in the forward direction for a given amount of incident optical power. Use of a laser is not critical; any directed, collimated beam of electromagnetic radiation with sufficient intensity can also achieve the effect. In fact, as will be seen in one embodiment, a less collimated, isotropic light may be desirable in some instances where the matrix material of the porous medium allows a certain amount of light to pass. Use of the collimated light is preferable, however, when the matrix material is naturally occurring, such as sandstones, as opposed to synthetic, such as glass beads. Collimation of an isotropic light source can be achieved by any of several means known in the art, such as lenses for focusing or parabolic reflectors. Where a laser is used, the polarization state of the laser (i.e., either random or linear) is not important for application in this invention. However, the same polarizing state should be used throughout where data from one application is to be correlated to data from a similar application. The wavelength of the light used is not restricted to a specific value, and can vary from the extreme infrared (IR) to the extreme ultra-violet (UV). However, since different wavelengths give different degrees of transmission for different applications, some wavelengths may be preferable over others. The choice will depend on the individual application. The criteria for selection is to choose the wavelength that is the most suitable for a particular application. "Suitable" includes such factors as intensity of light transmitted, dynamic range of transmission values, filtering effect of natural coloration in the porous medium, and possible grain size range of the medium. L. F. Gate has discussed the effect of frequency on diffusive transmission (The Determination of Light Absorption in Diffusing Materials by a Photon Diffusion Model, J. Phys. D: Appl. Phys., 4, 1049, 1054, 1971 [Great Britain]) and provides data indicating that light scattering, and hence transmission, through porous media is a function of the wavelength of the light as well as the natural coloration of the medium. Wavelengths that are at least one order of magnitude smaller than the mean grain diameter are preferred, and more preferred are wavelengths two to three orders of magnitude smaller than the mean grain diameter. In light of these criteria, the laser should be an ideal instrument for measuring small scale permeability variations in porous media of macroscopic thickness. In the following discussion, the word "laser" will be used to describe the light source, but this should not be understood as precluding the use of other sources of vectored, electromagnetic radiation which qualify under the above discussed selection criteria.

In the first embodiment of the invention, the laser is used to measure permeability of a porous medium. One requirement is that the individual grains of the medium not be opaque to the light being used. This requirement allows the invention to include naturally occurring media such as those found in geologic formations, such as sandstone, and artificial porous media such as sand or glass bead packs. In one example of this embodiment, the porous medium is Boise sandstone. The first step is to determine the correlation between light transmission through the medium and the permeability of the medium for a given fluid. Note that the fluid saturating the medium to facilitate the optical measurement is not necessarily the same as the hydraulic fluid for which the permeability is being determined. One means of determining this correlation is by measuring permeability of several homogeneous cores by classical means (flooding), then measuring the corresponding light transmission through a macroslab of the corresponding core, plotting light transmission versus permeability, and determining, by any of several means known in the art, a function which fits the plotted data. This function can then be used to convert light transmission readings to permeability for additional samples of unknown permeability. Alternately, the function can be plotted to establish a calibration curve; this curve should be valid for any core taken from the same formation (i.e., the same rock type). This assumption is valid as long as the index of refraction and clarity of the formation particles remain fairly constant, and the permeability variation results from grain size variation and not, for instance, a clogging of the pores by clays, or migration of fine particles clogging the pore throats. These latter affects will be discussed below.

Specifically, several small cores (known here as "calibration cores"), approximately 1" diameter by 1" long, from the same formation are obtained. At least six calibration cores should be used, and preferably 10. However, the ideal number is a number of cores which will give statistical significance to the data obtained therefrom. That is, once the data have been curve fitted, a statistical variance can be determined to see how well the curve fits the data. Depending on the accuracy desired for the final readings, if the curve does not satisfactorily fit the data, more data should be obtained to refine the population used to fit the curve, or to determine if a different type of curve should be fitted to the data. If the primary interest is in permeability variation and not absolute permeability measurements, then the curve will not need to fit the data as closely.

The calibration cores should be homogeneous as to permeability, with no variation of permeability across the sample. One means to determine homogeneity is by microscopic examination of a thin section of the calibration core, a method well known in the art. Alternately, since it is now known that laser light attenuation through a macroslab of a porous medium such as sandstone is dependent on the same variables as permeability, i.e., grain geometry, a macroslab, or a section between 1 and 20 mm, and preferably between 5 and 10 mm, of the calibration core can be obtained after the permeability is measured by flooding. A laser beam can then be projected through this core section at several points and the transmitted light measured at the other side of the section. If the transmitted light is not seen to vary from location to location across the core, then the calibration core is homogenous. However, if the transmitted light does vary, then either the data from that core should be rejected, or several light transmission readings should be taken at several different points of the section and averaged to obtain a light transmission number to correspond with the measured bulk permeability of the original calibration core. If any core section exhibits a color variation, then it should preferably be excluded from the calibration data.

A second consideration in selecting the number and type of samples to be used in developing the correlation function is that the samples should include permeabilities near the high and low ends anticipated in the formation. This will prevent potential erroneous results from extrapolation into regions where there is no data to provide support. Ideally the thickness of the sections used to establish the calibration curve should be the same as the sections whose permeability is to be measured. However, this does not preclude the possibility that results from a test section of a thickness different than the calibration section could not be correlated. For example, by scaling up or down proportionally, corrections for thickness might be made. In establishing the correlation between light transmission and permeability for calibration purposes, even in a "homogeneous" sample several light transmission readings should be taken and averaged. The reason for this averaging is that on some scale even "homogenous" materials become heterogeneous. For example, due to the small diameter of the laser beam, it is possible that the laser may impinge on a surface irregularity detectable on the beam-diameter scale (<1 mm) which is undetectable on the desired mapping scale (>1 mm). This would give erroneous results for purposes of calibration.

Note that the assumption is made that the porous media being investigated are nonreactive to the type of fluid present in the pores. It is well known that some porous media, especially clays, will react with different fluids to change permeability. Thus, a core which might have a permeability of 500 millidarcies (md) when flooded with a 5% brine solution will only have a permeability of 75 md when flooded with fresh water. To test for non-reactivity, one core from the formation should be flooded with a variety of fluids in core flooding permeability tests. If the permeability does not change with the fluid beyond that mathematically predicted from the fluid properties alone, such as viscosity, then the porous medium is nonreactive, and the calibration curve will not be reactivity-dependent. The fluids used in the reactivity test should include oil (preferably a white oil so that light absorption is not a factor), brine (a brine similar to the brine found in the formation is desirable), fresh water, and air. If the core is found to be reactive to different types of fluids, then the calibration curve will need be developed using only one type of fluid, and should be restricted to measurements of cores that are saturated with that particular type of fluid.

Once the calibration curve has been established to a statistically satisfactory level, and an accompanying correlation function has been determined by curve fitting means to the data, permeability of a macroslab can be measured by use of a laser for any core within the same formation. In the example described, five 1" diameter by 1" long cores with different, yet homogeneous, permeabilities were measured for their air permeabilities. Laser light was then transmitted through a 5 mm macroslab of each core and the light transmission measured. The data from these measurements gives the correlation curve of FIG. 1. While there is not a smooth correlation to the data, it should be noted that only five points have been plotted, and with the exception of point "B" of FIG. 1, a fair correlation does exist given the small data set used.

Generally, the core is not limited in maximum diameter, but should probably be no smaller than 1 cm in diameter. The method is preferably carried out in a dark environment to avoid spurious light which may affect the results. The section should preferably be between 1 and 20 mm and more preferably between 2 and 10 mm thick. The section should be mounted with one face facing the laser and the other face facing the light detector. Although in the preferred embodiment the section is mounted with its face at 90% to the direction of the laser beam and parallel to the light detector, these angles are not critical. However, the geometry for the test apparatus should be the same as the geometry of the calibration apparatus. If the geometry is different, however, mathematical corrections could be made utilizing the variation in geometry and the trigonometric relationship therebetween. The preferred embodiment envisions one laser and one detector in general alignment along a line perpendicular to the face of the section when the laser and the detector remain static with respect to each other. In the preferred embodiment, the laser and the detector are static while the core section is moved through the laser beam until the desired area to be scanned has been completely covered. However, it would be possible to use a small bundle of multiple detectors generally aligned with the laser, as distinguished from a single detector, with the multiple detectors coupled to an averaging device. Alternately, in the preferred embodiment, the core section could be static while the laser and detector(s) are dynamic with respect to the section and move across the face of the section to be surveyed. In a variation on the preferred embodiment, a moving laser and a static array of detectors (with respect to the section) spanning the area of the section to be scanned could be used. In still another variation a static laser is used with respect to a moving detector array and section.

With reference to FIG. 2, in one example the workpiece (1), a water saturated core section 5.5 mm thick and 10 cm in diameter, was scanned with a beam (2) from a 10 milliwatt, 632.8 nm wavelength, Helium-Neon laser (3) with random polarization and 0.68 mm beam diameter. The section was placed in a glass dish (4) and immersed in a bath of water (5). Typically the fluid would be either that found naturally in the section (to preserve its natural properties, as discussed above), or a fluid which might be injected into the formation, such as fresh water or brine in a water flooding operation in an oil field. In the example being discussed, the laser was located approximately 50 mm from the first side of the core. This distance is not critical, however, since the laser beam is highly collimated and does not diffuse over long distances in air. If dust or mist were present in the environment in which the test was being conducted, then the distance from the laser to the section would be more important. In the example the detector (6) was located within 2 mm of the other side of the section. Generally the detector(s) should be located as close as possible to the section since the light emitting from the detector side of the section is diffuse due to diffusion caused within the section. In this example a single static laser was used with a single static detector, while the section was dynamic. The detector area used was 1 cm×1 cm. The section was scanned in an up and down pattern with readings of the light transmission at the detector recorded at 1 mm intervals, starting with one extreme edge of the section. The section was then shifted 1 mm to the opposite edge, and readings recorded as the section was again scanned in an up and down pattern. This process continues until a grid has been formed scanning the complete section in all directions. While grid spacing of 1 mm×1 mm was used in this example, larger grids may be desirable if less resolution is required.

Smaller or larger detectors may need to be used as a compromise between sensitivity and spatial resolution. Additionally, detectors with higher or lower sensitivities may be required depending on the amount of light transmitted through the section and the capabilities of the signal conversion and recording devices used in the experiment. Since the amount of light transmitted is not only dependent on the properties of the section but also on the geometry of the experiment and equipment being employed, both of which are at the discretion of the experimenter, no absolute detector selection criteria can be formulated.

Typically the detector readings are analog voltages. These analog readings can be stored by any of several means known in the art, or can be converted to digital signals by an A/D converter (7) and stored as a recorded value in any digital data collection device, such as a computer (8). In this experiment the data was converted to a digital signal by means of a digital voltmeter and then stored in a Hewlett Packard desktop computer.

The recorded values obtained can then be displayed graphically to give a "map" of the light transmission through the section at any given point. Since light transmission can be correlated to permeability, this "map" will give a representation of the permeability variation of the core across the section. Alternately, if a mathematical curve fitting formula has been determined for the correlation curve, the recorded values can be applied to this formula, and a "map" of the absolute permeability across the section can be plotted. Alternately, the data could be displayed in a tabular form or used for further calculations.

In a variation on the first embodiment, the invention is used to measure the change in permeability of a core section as a function of time. Such a change can occur for instance where clay is present in the core section. As discussed earlier, often these clays will swell when saturated with fluids other than the natural reservoir fluid. An apparatus for making such measurements is shown in FIG. 3. The workpiece core section (1) is placed in a clear, watertight container (11) having fluid inlet (12) and fluid outlet (13). A photodetector (6) as shown in the first embodiment is placed preferably adjacent to the side of the container (11) against which the section rests. The laser beam (2) from the laser (3) is impinged on the side of the section opposite the detector. The laser and the photodetector are preferably approximately aligned. The photodetector measurements are recorded either on a chart recorder (14) or by a computer or data logger so that the readings can be correlated to a time measurement. Other means of accomplishing this objective of recording coincident time values and detector measurements which are known in the art can be applied. Initially, in recording these time values and detector measurements, the container and section are flooded with a fluid F1 and the light transmission through the section is measured in this base state. At time t=0 a second fluid F2 is introduced into the container by way of the inlet (12). The second fluid displaces the first fluid out of the container through the outlet (13). The measurements from the photodetector are recorded starting at time t=0 and continuing until a steady state is reached or the experiment is terminated. The recorded values will be correlatable to the permeability, as taught in the discussion above for the first embodiment, and will indicate how permeability changes over time as the clay in the section swells or contracts. Although the apparatus disclosed only measures light transmission at one point on the section, the method herein described can be applied at various points on the section. Additionally, by first mapping the permeability of the section as described in the first embodiment, variations in the base state permeability can be accounted for when monitoring the change over time in permeability at various points on the section after flooding with the second fluid.

The time dependent reduction of permeability can result from mechanisms other than clay swelling. Specifically, the migration of fine intergranular particles under the influence of flowing fluid can cause the particles to collect in the pore throats, reducing fluid flow and thus permeability. Thus the above variation on the first embodiment could be used to measure the reduction of permeability as a function of time due to the migration of fine particles. An apparatus similar to that shown in FIG. 3 can be used with the modification that the fluid inlet (12) and outlet (13) are oriented on the top and bottom of the chamber (11), respectively.

In a second embodiment the invention described can be used to measure grain size and grain size variation of porous media. The configuration to determine grain size is identical to the configuration described above for permeability mapping. However, for this second embodiment, smaller detectors on the order of 2 mm×2 mm should be used. This invention makes use of the phenomenon that the laser beam, while a pinpoint on the incident side of the macroslab when first impinging said macroslab, appears as a luminous disk on the emergent side, with the maximum intensity at the center of the disk. The intensity in this disk will decrease as the distance from the axis along which the laser is projected increases. The distribution of light across the disk will have a typically Gaussian shape. In one example, numerical simulation of the effect was performed by computer. A three dimensional numerical simulation of ray propagation, using a stochastic approach, was used. In the simulation, a hypothetical light ray is traced as it propagates through the medium. As the ray is scattered, its intensity is reduced by the quantity of light reflected, and finally, if the ray emerges at the other side of the medium, its intensity is recorded. This is done for a very large number of rays, on the order of 1 million. In addition, the location at which the ray emerges is recorded.

The results of the simulation are shown in FIG. 4. The results have been visually verified and are consistent with the type of spreading pattern predicted by Genceli, (Measurement of size and concentration of scattering particles by speckle photography, J. Opt. Soc. Am., V70, 10, 1212) albeit for much lower particle densities, yet the same physical phenomenon. In the preferred embodiment correlation curves like that of FIG. 5 are first established either by numerical simulation or by measuring the actual emergent beam profiles of rock samples having known grain size. Once the correlation curves have been established, rock samples of unknown grain size can be tested and their emergent beam profiles recorded. These stored profiles of samples of unknown grain size can then be compared with the profiles of samples of known grain size, and the unknown grain size determined by suitable interpolation means known in the art.

Specifically, an apparatus for determining grain size of a porous composite would resemble that of FIG. 2. The similarity in apparatus is due to the fact that the grain size mapping embodiment is merely a subset of the permeability mapping embodiment. However, for grain size mapping the single detector (5) used for permeability mapping is replaced by a fixed array of detectors covering the entire area of the section to be scanned. Detectors having the smallest possible area are preferred, with minimal but discernible spacing between detectors preferably 0.1 mm or less. This will give high resolution, a desirable feature of this embodiment. Detectors having an area of 2 mm×2 mm are commercially available, as for example from Silicon Detector Corp. of Camarillo, Calif. As discussed in the first embodiment, various combinations of static and dynamic arrangements can be configured between the laser beam, the core section and the detectors. However, in the preferred embodiment the section and detector array are static with respect to a dynamic laser beam. Using automated means known in the art, a complete system can be created for mapping grain size of a core section as a function of the surface spatial coordinates of the section. Further, these measurements can be part of, and simultaneous with, the permeability mapping measurements described in the first embodiment. With reference to FIG. 6, the workpiece (1), a core section, is placed on a static array of detectors (20). The core is preferably saturated with a liquid such as water or white oil, and can be immersed in a bath of the liquid in a glass dish as in the example in the first embodiment. The glass dish and liquid are omitted from FIG. 6 for simplicity. The individual detectors (10a through 10in) of the array (20) are connected by leads [generally (21)] to an analog to digital signal converter (22), which sends the converted digital signal to a digital computer (23). The outputs of the individual detectors can be read individually or addressed more efficiently through a multiplexer known in the art. The digital computer (23) also controls a servo control mechanism (24) which in turn controls servo motors (25) and (26) which position the laser (3) by any of several means known in the art, such as the rack and pinion positioner (27) shown. The computer (23) is programmed to move the laser (3) in predefined increments in the horizontal and vertical directions (corresponding to x and y coordinates) until the entire core section has been scanned by the laser beam (2). At each position the laser (3) is held steady while the (x,y) coordinate position and the corresponding outputs from the detector array (20) is recorded by the computer (23). After the complete core section has been scanned the data recorded by the computer is processed to generate an output, which may be a graphical display (28). In the preferred embodiment the output is a qualitative topological "map" of the grain size. The amplitudes of the elevations in the map correspond to the full width at the half-power point of the emergent beam as recorded by the detectors, as demonstrated graphically by FIG. 8. Areas with finer grains will have wider distributions, and hence higher "peaks" in the topological map. Alternately, inverses of the emergent beam width could be recorded such that the "peaks" would correspond to larger grain sizes. As discussed in the above paragraph and similarly for permeability mapping in the first embodiment, the light transmission values themselves could be mapped to show relative variation in grain size as a function of location, or, given correlation data developed previously, actual grain sizes can be plotted as a function of location allowing development of a quantitative topological grain size map.

In a third embodiment of the invention, light transmission through a porous medium is used to determine the wettability of the medium. If a porous medium is saturated with a combination of two immiscible fluids, such as white oil and water, one fluid will preferentially coat the grains while the other fluid will fill the pore voids. The fluid coating the grains is known as the "wetting" fluid, and the phenomenon is referred to as "wettability". The affinity of the wetting fluid for the grains is a function of several variables, including the fluid properties and whether one fluid was present before the other. The invention makes use of the discovery that when the wetting fluid has an index of refraction closer to that of the porous medium particles than does the pore filling liquid, light transmission through the medium will approach the maximum. Alternately, when the pore filling fluid has an index of refraction closer to that of the porous medium particles than does the wetting liquid, light transmission through the medium will approach the minimum. This is due to the fact that at optical junctions (the interface between two immiscible substances having different refractive indices), the nearer the two refractive indices are to one another, the more forward scattering there will be. This embodiment can be used to determine wettability characteristics of a porous matrix such as a sandstone under normal reservoir conditions and how this matrix will be affected by changes in conditions, such as treatment with a surfactant.

Specifically, we start with a macroslab of, for example, dry sandstone of known weight having reasonably homogenous permeability. The porosity of the macroslab, which will be referred to as the "section", is first determined by means known in the art. The section is then saturated with a first fluid, for example, white oil, then weighed. A laser beam is then projected against one side of the section and the emergent beam power measured and recorded. The first fluid is then incrementally replaced with a second fluid, which is immiscible with the first fluid and having a refractive index different than the first fluid, for example, water. After each incremental addition of the second fluid the section is weighed and laser light transmission through the section is recorded. The second fluid is added until the weight no longer changes. In the water-replacing-oil case described here, this stage is known as the state of irreducible oil saturation. From the known porosity of the section, the known densities of the two fluids, and the recorded weights, the percent of each fluid in the section at any given weight can be determined. The data is then recorded and would resemble the upper curve (31) in FIG. 7. The process is then repeated by adding the first fluid to the section initially fully saturated with the second fluid and recording the weights and light transmission values. When this second set of data is plotted it will resemble the lower curve (32) in FIG. 7, in the case of oil-replacing-water. The complete FIG. 7 is now a calibration curve for wettability of this porous medium at normal conditions for the two fluids. Conditions can now be varied, for example, the section can be saturated with oil and then replaced with water which has been treated with a surfactant.

In one example of the embodiment, a slab of Boise sandstone 5 mm thick was first saturated with white oil having a refractive index of $n=1.45$. The refractive index of the sandstone matrix medium is that of quartz, $n=1.55$. The oil in the slab was then replaced with water with refractive index $n=1.33$, following the method described above, the laser power transmitted through the slab was measured and recorded at various states of saturation. Once the slab was fully water saturated (irreducibly oil saturated), the water was then flushed from the slab with the white oil, following the stepwise method described above. FIG. 7 shows the measured points, A, B, C and D, with interpolated upper curve (31) indicating the oil-wet grain condition and interpolated lower curve (32) indicating the water-wet grain condition. As discussed above, such a set of curves could now be used to determine what proportion of oil wet grains would become water wet if flushed with water containing a surfactant. A known volume of the surfactant containing water would be added to an oil saturated slab for which wettability curves such as FIG. 7 has been developed. The percent saturation "s" is known, the transmitted power "t" is measured, and point "x" is determined. This point indicates the portion of grains that have become water wet. If "x" falls closer to the upper curve, the sample is more oil wet than water wet. Consequently, if "x" falls closer to the lower curve, the sample is more water wet. The oil previously covering the grains is now free and recoverable. Information obtained by this method is useful in predicting oil recovery increases by use of surfactants in oil fields.

In the manner that permeability and grain size can be mapped as described above in the first two embodiments, similarly wettability can be mapped. This mapping would be preferably done when one fluid is replacing another, wherein several maps would be generated. In this manner the wetting characteristics of the porous material can be observed. By use of a computer, the change in wettability as a function of time could be calculated, and the change plotted to show a "wettability potential" map. The above method assumes that permeability is homogenous throughout the macroslab. However, if it is not, a permeability map can first be generated for a macroslab by the method of the first embodiment, and then corrections can be made for the wettability curves using that information.

Once the permeability for a core section has been determined by the method described in the first embodiment, and the grain size for the same section has been determined by the method described in the second embodiment, the porosity of the section can be calculated from the Kozeny-Carman relation, and the results can be mapped to produce a topological map of the porosity of the section. Thus the invention provides a complete system for measuring and mapping the petrophysical properties of porous media such as sandstones.

In a fourth embodiment of the invention, laser transmission through porous media can be used to determine the presence and type of fluid in the media pores. This combination of media and fluid may or may not be transparent to non-laser light. However, the embodiment assumes laser light will be used due to the collimated nature of the laser beam which will result in finer resolution of the medium characteristics. Further, this embodiment assumes that the medium has homogeneous permeability over the section surveyed. Finally, this embodiment further assumes the fluid is transparent to the light being used.

As previously discussed, if a porous section is flooded with a non-absorbent (to light) fluid of increasing refractive indices approaching that of the matrix material, light transmission through the medium is seen to increase. Further, as is well known in the art, as the number of optical junctions increases, the scattering increases, and light transmission decreases. An optical junction being a junction between two materials having different refractive indices. Finally, light transmission decreases as the light absorption of a fluid increases. That is, light transmission through a porous medium is a function of the index of refraction of the fluid, the number of optical junctions in the medium, and the light absorbance of the fluid. It is important to note what light absorbance is being considered, as some fluids may be more transparent to one frequency of light than to another. Due to this dependence of the light transmission on three independent variables, any method for determining fluid properties by use of light transmission through a porous medium containing the fluid will need to hold two of the variables constant. In this embodiment, it is assumed that the light absorbance of the fluid remains constant while either the index of refraction or the number of optical junctions vary. Thus, this embodiment has two variations.

Since homogenous permeability of the medium is required for this embodiment, an artificially fabricated medium is preferably used. However, naturally occurring media can be used, but their homogeneity should be first assured by the method described in the first embodiment. One means for fabricating the porous medium is to create a pack of transparent beads, preferably glass or quartz, and preferably irregularly shaped or having multiple surfaces to maximize the scattering effect. The pack will be referred to hereinafter as a "sand pack". However, as discussed, artificial "sand" can be used as well as naturally occurring sand. The choice of size of the grains to be used should be made so as to optimize the selection criteria; the choice is a compromise between 1) the stronger attenuating effect of smaller grain sizes, suggesting the use of larger grains; and 2) the larger sensitivity to fluid refractive index change for smaller grains, suggesting use of smaller grains. The sand pack can be fused together or simply contained in a chamber for the purpose of maintaining the structural integrity of the pack. The thickness of the sand pack will be a function of the particular application, and light transmission and dynamic range of the transmission should be the primary criteria for choosing the thickness. The attenuating effect of the grains highlights the advantage of the porous medium approach over an approach where the refractive index of the fluid alone is monitored. In the former approach, there is a much higher sensitivity of the transmitted light to changes in refractive index of the fluid than in the latter approach.

In the first variation, the index of refraction of the fluid filling the pores of the medium varies. One method by which this can occur is if two miscible fluids having different refractive indices are mixed, resulting in a fluid with an index of refraction different than either of the individual fluids. An example of such a mixture is toluene and water. This variation could be used to detect contamination of one fluid miscible with another having a different index of refraction. An apparatus for accomplishing this is shown in FIG. 8. With reference to FIG. 8, in this example a porous medium (41), fabricated from transparent beads (42), is contained in a chamber (43) which is used to conduct the fluid (45) to be monitored or a slipstream thereof. The chamber has at least two opposing points (44a) and (44b) which are transparent. The remainder of the chamber is preferably opaque to minimize light propagation within the walls of the chamber to the detector. The beam of collimated electromagnetic radiation (2) from the radiation source (3) used to monitor the fluid is projected through the transparent portion of the chamber to a light detector (6) adjacent to the chamber. The output (46) from the detector can be used for any number of functions. For example, it can be connected to an analog output indicator (47), converted to a digital signal and further processed, or coupled to an electrical switch to activate an alarm or other device. As the fluid passes through the chamber the amount of laser light which is transmitted to the detector will vary as index of refraction of the fluid varies. One example of an application would be a chemical manufacturing process where contamination is possible, as for example in alcohol manufacturing where water contamination can occur. A slipstream of the production stream could be diverted through a chamber as described above and checked for variation of the index of refraction with the laser as described. If the index of refraction varies beyond a predetermined acceptable level, the output from the detector could be used to signal an alarm or shut down the process.

Another application of the variation of this embodiment would be to use the output signal to calculate the percent of contaminating fluid present. If the amount of light transmitted through the medium when fully saturated with each liquid is known (by measurement), and then the light transmitted in a mixture of the two liquids is measured, mixing laws known in the art can be used to calculate the percent of each liquid present in the mixture. This variation and its applications and examples could find uses in chemical, petrochemical, pharmaceutical, food and other manufacturing processes.

A second method by which the index of refraction of the fluid saturating the medium can vary is if the medium sees different fluids with different refractive indices at different times. For example, in a phase separation process in which two or more fluids with different densities and different refractive indices are allowed to settle out in a vessel and are then pumped out of the vessel, the embodiment could be used to detect the presence of the different fluids in a common pump out line. The output from the detector cell could then be used to switch a directional valve to isolate the different fluids into different storage vessels. In one example of this variation of the embodiment a non-reactive sand pack of uniform permeability was saturated in turn with toluene (index of refraction n=1.49), with water (n=1.33), and air (n=1.0, i.e., the sand pack was dry).

After each saturation, the laser light attenuation through the macroslab was measured, with results shown in FIG. 9. As FIG. 9 indicates, the general shape of the curve plotting attenuation as a function of grain size of the medium remains essentially the same for the three saturating fluids (curves 1, 2 and 3). However the experimental results indicate that the attenuation curve shifts upward to a less attenuated region (i.e., towards less negative values) as the index of refraction "n" of the saturating fluid increases. In a medium with constant grain size, if the attenuation is a known measured value then given a set of curves similar to those of FIG. 9, and assuming constant light absorption of the fluid, the index of refraction of the fluid saturating the medium can be determined. If only a few saturating fluids are possible, each with a distinctive index of refraction, then the saturating fluid can be identified. FIG. 9 also shows that smaller grain size of the medium will result in greater sensitivity, i.e., greater differences in attenuation for two fluids having different refractive indices. In the example discussed, the attenuation rather than light transmission was the recorded value. Attenuation as a recorded value is defined as $$Attenuation = 10.0 \log (P_2/P_1) \, dB$$

where $P_1$ is the power transmitted through a sand pack of one thickness and $P_2$ is the power transmitted through a sand pack of the same grain size, but a different thickness, where each sand pack is contained between two glass plates. Recording the attenuation in this manner cancels the effects on the transmission of the glass plates, and thus the effect of the medium itself can be isolated. This is desirable if experimental results are to be compared with theoretical results.

The experimental results of FIG. 9 are verified by a three dimensional numerical simulation of ray propagation, as described previously, using a stochastic approach. In the simulation, a hypothetical light ray is traced as it propagates through the medium. As the ray is scattered, its intensity is reduced by the quantity of light reflected, and finally, if the ray emerges to impinge on a detector at the other side of the medium, it's intensity is recorded. The results of one simulation are shown in FIG. 10. The simulation generally verifies the experimental results that show that attenuation of light increases (i.e., light transmission decreases) as particle size decreases and as index of refraction of the saturating fluid decreases.

In the second variation of the fourth embodiment the number of interfaces in the medium varies while the other factors affecting light transmission remain constant. This can occur if two immiscible fluids such as air and water or oil and water mix in the porous medium, or if two phases of two single substances are present, such as steam and liquid water. The mixture will create new optical junctions where the two immiscible fluids meet, creating additional scattering in the medium. The increase in the number of junctions will decrease light transmission, and thus the presence of, or the variation in, the quantity of an immiscible fluid can be detected as a result of this decrease in light transmission. An apparatus similar to FIG. 8 can be used for this variation of the embodiment as well. One example of an application for this variation is a petroleum refining process where water is stripped from white oil. If oil becomes entrained in the water, an undesirable effect, the presence could be detected by an apparatus similar to FIG. 8 which would be installed in an outlet line from a condenser unit condensing the stripped water. The output from the detector could then be used to sound an alarm or adjust the process.

In a fifth embodiment of the invention, a fluid saturated porous media on a larger than core scale but still on the scale of a laboratory model can be used to model fluid flow behavior in porous structures. This embodiment is useful for laboratory scale model simulation of complex systems and can be used in conjunction with computer simulation programs to verify results and predictions. The embodiment has the advantage over other flow modeling techniques in that hydraulic flows are not required, significantly simplifying the modeling apparatus. In its broadest form, the system to be modeled is reproduced on a scale version, with regions or zones of differing permeability created from artificial sand or glass bead packs with particle sizes preferably in the 100–1000 μm range. The mean diameter of the grains of the medium should vary no more than does the mean diameter of the reservoir being modeled. One or more light sources is then located within the model to simulate fluid sources, and light detectors are located within the model at points at which fluid flow information is desired. Alternately detectors could be located at transparent model boundaries. The signals received by the detectors will correspond to the fluid flow at the detector locations in an equivalent steady state flow model, in view of the previous discussion of the effect of particle size on permeability and light transmission.

An example of an application of this embodiment is modeling fluid flow in a petroleum reservoir. The model can be constructed to either replicate conditions in a known reservoir using information obtained from cores taken from the reservoir, or the model can simulate a hypothetical reservoir. Because the transmitted light from an isotropic source will be attenuated in the model reservoir within a very short distance (due to the diffusive attenuation as well as the geometric spreading of light), it may be desirable to use glass beads since they permit more light transmission than quartz grains. The reservoir permeability variation is then reproduced as closely as possible by using different layers of different bead sizes. The beads may be mechanically bonded to one another if desired by sintering, clear epoxy, or other means. In an experiment where steady state flow characteristics of the reservoir are the desired parameter to be modeled, the model should be flooded with a liquid that will enhance the light transmission. The fluid should be clear and preferably non-absorbent to light (i.e., "water white"). The index of refraction of the fluid should be selected based on the criteria previously discussed in the first embodiment. The simulation can be enhanced by modeling the movement of a fluid interface within the reservoir. For example, if one fluid is used in actual field applications as a "drive" fluid, either by natural presence (such as ground water or a gas cap) to drive oil toward a production point, this event can be recreated in the model by adding means for injecting a second fluid, having a different refractive index, into the model to "drive" the first fluid with which the model is initially flooded. As a result, some of the light traveling from the light source to the detector will be reflected at the fluid interface, and not arrive at the detector. Upon arrival of the fluid interface at the detector, the amount of light arriving at the detector will change, and the occurrence of the interface arrival can be noted. While this variation may not provide information regarding flow quantities, it can be useful in predicting dynamic, evolving flow patterns, particularly if several detectors are located throughout the model. Additionally, data collected before the arrival of the fluid interface at the detector can provide valuable information.

As an illustration, FIG. 11 shows an apparatus in Diagram A where a permeable zone generally indicated by (51) with of length D being isolated between two impermeable barriers (52) and (53). A light source (54) is isolated from the permeable zone (51) by a glass tube (55). At the opposite side of the zone from the light source the zone is isolated by a clear wall (56). A light detector (6) is pressed flush against the wall (56) opposite the permeable zone (51). The permeable zone is first saturated with an initial fluid F1 having index of refraction $n_1$. A second fluid F2 with index of refraction $n_2$ is added to the zone by means of a very small transparent injector such as the nozzle (57) which does not interfere with the optical measurement. It is assumed that $n_1$ is not equal to $n_2$, and that F1 and F2 are immiscible. Means to allow fluid F1 to escape as fluid F2 is added is provided, such as the outlet tubes (58) and (59). As the fluid F2 is injected, the interface (I) is created next to the interface ($I_1$), and moves towards the detector (6). The region ahead of the interface (I) is fully saturated by fluid F1, and the combination of fluid F1 and the matrix material of the porous medium (51) will be referred to as Medium 1. The region behind the interface (I) is filled partly with fluid F2 as it is injected and partly with fluid F1 (i.e., some residual fluid F1 remains behind interface (I) as fluid F2 is injected). This combination of fluids F1 and F2 as well as the matrix material of the porous medium (51) will be referred to as Medium 2. The application consists of recording the power "P" of the light received at detector (6) as a function of time "t", commencing at t=0 when the injection of fluid F2 begins. The recorded result would resemble Diagram B of FIG. 11 in the case where $n_1 > n_2$, and $n_1$ and $n_2$ are less than the refractive index of the matrix medium. From Diagram B we can develop Diagram C, which gives the location of the interface (I) as a function of time, and thus also gives the velocity of the interface. An example where this information is useful is in the injection of water into a subsurface hydrocarbon bearing reservoir. By knowing the fluid interface velocity and position, well performance can be predicted. Since P is known (by measurement), the distance "d" of Diagram C is determined from Equation A:

$$P = T_o A_d G(d) \Gamma_a \Gamma_I \Gamma_b \left( \exp\left[ \frac{-d}{l_2} - \frac{D-d}{l_1} \right] \right)$$

where
$T_o$ = the optical power incident per unit area of the interface ($I_1$), which can be determined from the properties of the source light (54);
$A_d$ = area of the face of the detector (6);
$G(d)$ = the geometric spread factor for light as a function of $d = r_o/d$ ($r_o$ and $d$ as defined in FIG. 11);
$\Gamma_a$ = the power reflection coefficient at the interface ($I_1$);
$\Gamma_I$ = the power reflection coefficient at the interface (I);
$\Gamma_b$ = the power reflection coefficient at the interface ($I_2$);
$l_1$ = the photon mean free path in Medium 1;

$l_2$ = the photon mean free path in Medium 2.

Equation A is solved for d by the following method: Since the relationship between P and t is known graphically (FIG. 11B) a value for d is selected, P is calculated from Equation A, and time t from FIG. 11B that corresponds to the calculated P is determined, a plot of d and t is then made. Successive iterations of this process with different values of d, then interpolating a curve between the plotted points, will yield the d versus t curve.

As an illustration of the application of Equation A, with reference to Diagram B of FIG. 11, if fluid F1 is white oil having index of refraction $n_1$ and fluid F2 is water having index of refraction $n_2$, at time t=0 the entire zone (D) of Diagram A is oil-saturated, and the detector (6) reads a power level $P_1$. In this illustration, it is assumed that $n_1 > n_2$, but this is not a requirement, and the only restriction is that $n_1$ is not equal to $n_2$, and $n_1$ and $n_2$ are less than the index of refraction (n) of the matrix material. At t=0, $\Gamma_a = \Gamma_b = \Gamma_1$, where $\Gamma_1$ is the power reflection coefficient for Medium 1. The value of $\Gamma_1$ can be determined from a separate reflectance measurement method known in the art. As soon as the first small volume of water is injected by the injector (57) a very thin layer of Medium 2 forms around the glass tube (55). At that time the power P will suddenly change to $P_2$ of Diagram B due to the replacement of $\Gamma_1$ with $\Gamma_2$, the power reflection coefficient for Medium 2, and the introduction of interface (I), and thus the term $\Gamma_I$ in Equation A. Following this initial event the power P then drops more gradually as shown in Diagram B as fluid F2 is added and fluid F1 is displaced. When the interface (I) gets very near the interface ($I_2$) (i.e., d≃D), the power will be at $P_3$ of Diagram B. At the point where Medium 2 bridges the gap to the interface ($I_2$) at the glass wall (56), the power will jump to $P_4$ of Diagram B. This jump is explained by $\Gamma_b$, which prior to the bridging was equal to $\Gamma_1$, now becomes equal to $\Gamma_2$, and the elimination of interface (I), and thus the term $\Gamma_I$. Following the bridging event there will be no further change in P, since at that time an optically static system exists. In light of this discussion and diagrams A and B of FIG. 11, the solution to Equation A can now be solved for d since we know that $$P_1 = K\Gamma_1^2 \left[ \exp\left(-\frac{D}{l_1}\right) \right]$$

$$P_2 \approx K\Gamma_2\Gamma_I\Gamma_1 \left[ \exp\left(-\frac{D}{l_1}\right) \right]$$

$$P_3 \approx K\Gamma_2\Gamma_I\Gamma_1 \left[ \exp\left(-\frac{D}{l_2}\right) \right]$$

$$P_4 = K\Gamma_2^2 \left[ \exp\left(-\frac{D}{l_2}\right) \right]$$

$$\Gamma_I = \sqrt{\frac{P_2 P_3}{P_1 P_4}}$$

$$\Gamma_2 = \Gamma_1 \Gamma_I \left(\frac{P_4}{P_3}\right)$$

-continued $$l_1 = D \ln\left(\frac{P_1}{K\Gamma_1^2}\right)$$

$$l_2 = D \ln\left(\frac{P_4}{K\Gamma_2^2}\right)$$

where

K = $T_o A_d$ G(D), a constant for a given apparatus.

Additional helpful information can be obtained by measuring the volume of the effluent of fluid F1 from the apparatus as a function of time.

The above example is only one illustration of how fluid flow modeling can be conducted utilizing the present invention. Further refinements of the analysis is possible by one skilled in the art. Starting from this example, more complex models having different geometries can be developed.

In modeling the reservoir, the zones should be contoured to replicate undulations or discontinuities in the reservoir itself. FIG. 12 shows in cross section one example of a model fabricated to simulate fluid flow in a petroleum reservoir. A clear glass vessel (61) approximately 15" in diameter and having straight sides approximately 12" high was used to simulate the reservoir. The bottom of the vessel was internally lined with black epoxy (62) to act as a light seal. A tempered clear glass tube (63) was sealed to the bottom of the vessel with caulk (64). The top portion of the tube protruding above the uppermost layer of sand is coated with black tape or epoxy (65) to act as a light seal. A tubing (66) of ¼" diameter plastic is run down the inside of the vessel (61) to provide a means for emptying fluid from or adding fluid to the vessel. A first layer of relatively impermeable sand (67) with a mesh size between 140 and 270 was deposited in the vessel. Further layers of differing grain size were deposited to test certain theories in experiment, as explained below. The complete reservoir model was filled with a fluid (68) (water) before the tests were run to improve light transmission. A highly compact, high intensity white light should preferably be used as the light source. In the example being discussed, a Sylvania 750 W tungsten halogen lamp (69), suspended from an electrical supply cord (70), was used as the source light. Because of the heat generated by the intense heat a cooling means such as a fan or blower may need to be employed to keep the light bulb from overheating and prevent possible damage to the reservoir model. Alternately, the light can be activated for only short periods of time if heat is a problem. In the example, short lighting periods were used. Although the results were only visually noted in the experiments, detectors (71) through (81) could have been placed adjacent to the vessel at the different zones and measurements taken. A top zone of relatively impermeable fine sand (82) with a mesh size between 60 and 80 is used as a light seal.

In a first experiment, a layer of relatively permeable glass beads was used to test whether diffusively propagating light would be confined to high permeability channels and not spread out along the vectors (100a-100e), and further, whether it would follow the path shown by the vector (101) and not be impeded by the contour (83) as it would if it merely followed the path shown by vector (102). One side of this layer (84) is left flat and the other side (85) is contoured. The bead diameters for this layer ranged between 1.0 and 1.05 mm. Results demonstrated that light did follow the path of vector (101). Although the light at the vessel adjacent to section (85) was not as intense as the light adjacent to section (84), this can be explained by the greater path length that light must travel in following vector (102) over vector (101) and the resultant increase in diffusion.

In a second experiment utilizing the apparatus of FIG. 12, the previous experiment was isolated by a region of relatively impermeable glass beads (86a) and (86b) having bead diameters between 0.10 and 0.11 mm. Permeable zones of glass beads (87a), (88a), (88b) and (87b) were deposited along with an impermeable annulus barrier (shown in cross section by (89a) and (89b)). Bead diameters for zones (87a,b) were between 0.45 and 0.50 mm. Bead diameters for zones (88a,b) were between 1.00 and 1.05 mm. Bead diameters for zones (89a,b) were between 0.10 and 0.11 mm. The purpose of the experiment was to test whether light would follow expected fluid flow paths and move along vector (103) into zones (87a) and (87b) and not flow into zones (89a) and (89b). Light propagation along vector (104) is generally anticipated. The visual results show that light will indeed "flow" through the permeable zones in a manner simulating the flow of fluids. Specifically, a bright light was observed at the vessel wall adjacent to zones (88a) and (88b), a less bright light was noted adjacent to zones (87a) and (87b), and virtually no light adjacent to zones (89a) and (89b). The difference in light between zones (87a,b) and (88a,b) can be explained by the somewhat lower permeability of zones (87a) and (87b) compared to zones (88a) and (88b) and also the longer path length the light needs to take in following vector (103) and the resulting loss due to diffusion.

The above results demonstrate the similarity between diffusive propagation of light and fluid flow which forms the basis of the fifth embodiment of the invention. In the dynamic model illustration discussed above where one fluid replaces another, this similarity extends further to include the similarity between the fluid front itself and a "light front" at the interface between the two fluids that moves along with the fluid front.

In fabricating reservoir models, source points simulating either natural reservoir resources or artificial source injection points can be included in the model by placing glass tubes at the desired source locations. That is, more than one source light may be used. In fact, when simulating natural in-situ resources, several source points should be used to simulate a broader distribution of fluid source. When an artificial source such as water or steam injection is to be simulated, the number of actual source points should be replicated in the model. Production points simulating points at which fluid is to be extracted from the reservoir can be simulated in like manner by placing glass tubes at the desired locations within the model and placing detectors inside these tubes. Production points are not necessarily points at which fluid is to be extracted, and may merely be points at which fluid flux is desired to be known. Additionally, a source point can act as a production point, and vice versa. Within a glass tube, a light source or a detector can be moved up or down to simulate injection or production at various depths within the reservoir. The signal from the detectors can be converted (analog to digital) and recorded. The results can be used for such purposes as estimating fluid production at a point, determining flow patterns in a reservoir, determining optimal location of steam or water injection wells, and determining the optimal depth at which to produce from a reservoir within a given well.

An illustration of a reservoir model incorporating the above features is shown in FIG. 13. The reservoir model, shown generally by (110) is comprised of various layers (11a–11d) of varying permeabilities made up of sand or glass beads. Although not shown for simplicity, the layers would be confined by a vessel enclosing at least the four sides and bottom of the reservoir model. The reservoir model is fitted with a fill line (66) so that liquids may be added to the model and a drain line (112) for extracting liquid or draining the model. The layers (111a–111d) are contoured to simulate the conditions to be modeled. Within the model are several glass tubes (113a–113h) closed at the bottom and open at the top above the uppermost layer (111a). These tubes can either be production points or source points, as discussed above. In the illustration, tube (113f) acts as a source point and has a bright isotropic light (69) suspended from electrical supply lines (70) acting as a source of simulated fluid. Tubes (113d) and (113e) act as monitoring points and have light detectors (114) and (115) inserted in them. Tubes (113a), (113g) and (113h) can be painted flat black to absorb light and simulate production points. The shadowed regions behind these black tubes simulate real-world reservoir conditions where the fluid flow is similarly distributed at production points. The detectors send a signal proportional to the light received at the detector to a meter or recorder (not shown) via leads (116) and (117), respectively. These detectors can be located at different depths within the tube to determine the variation in simulated source fluid as a function of depth within the model. For example, by use of a servo (118) connected to detector (115) by the detector leads (116), the position of the detector (115) can be varied within the tube (113e). The position of the detector (115) and the corresponding light reading could be recorded by a recording means, as for example the strip-chart recorder (119), or could be sent to a computer (23) for further processing. While the isotropic light (69) provides one means of simulating the source, an alternate means would be a laser. In this variation a laser (3) generates a coherent beam of radiation (2) which is projected down the glass tube (113b). A mirror (120) located within the tube is angled so as to reflect the beam in a vectored direction as shown by vector (121). The benefit of using the laser as the simulated source is that much greater transmission distances can be achieved. It should be observed that actual fluid injection points such as described in FIG. 11 can be incorporated into the type of model shown by FIG. 13 to collect data from moving fluid interface modeling.

While the above embodiments of the invention discuss use of an essentially continuous light source, it will be observed by one skilled in the art that the measurements discussed above can be performed in the time domain by using a pulsed light or a pulsed laser and an optical oscilloscope.

From the above description it is evident that the present invention provides a method and apparatus for measuring properties of porous media by use of light or laser transmission through the media. Although only specific embodiments of the present invention have been described in detail, the invention is not limited thereto but is meant to include all embodiments coming within the scope of the appended claims.

What is claimed is:

1. A permeability mapping apparatus comprising:
   (a) a matrix medium of closely packed particles;
   (b) a pore filling medium symbiotically interposed within said matrix medium;
   (c) a means for generating a coherent collimated beam of electromagnetic radiation, said beam of electromagnetic radiation vectored to transpierce a series of locations defining said matrix medium;
   (d) a means for successively generating an attenuation signal for each of the vectored beams of electromagnetic radiation at each location transpierced by said beam of electromagnetic radiation, and assigning a weighted value based on a correlation function of known permeability to each of the attenuation signals so as to compensate each beam attenuation signal for attenuations at other than one of said matrix locations;
   (e) a means for reconstructing all said weighted values over said series of locations defining said matrix so as to reconstruct said matrix in terms of each attenuation signal at each of said locations;
   (f) a means for displaying each reconstructed value to image said matrix medium.

2. The apparatus of claim 1 wherein the matrix medium is embodied in a compartment, said compartment having a means for allowing both ingress and egress of electromagnetic radiation.

3. The apparatus of claim 1 wherein the pore-filling medium has a refractive index greater than the matrix medium.

4. The apparatus of claim 1 wherein the pore-filling medium has a refractive index less than the matrix medium.

5. The apparatus of claim 1 wherein the matrix medium and pore-filling medium are optically transparent.

6. The apparatus of claim 1 wherein the matrix medium and pore-filling medium are optically translucent.

7. The apparatus of claim 1 wherein the means for generating a coherent collimated beam of electromagnetic radiation is a laser source.

8. The apparatus of claim 1 wherein the means for generating a coherent collimated beam of electromagnetic radiation is a parabolic reflector and lens combination used in conjunction with an isotropic light source.

9. The apparatus of claim 7 wherein the wavelength of the electromagnetic radiation is at least one order of magnitude smaller than said matrix medium's mean grain diameter, preferably said wavelength being two to three orders of magnitude smaller than said mean grain diameter.

10. The apparatus of claim 9 wherein the matrix medium is Boise sandstone.

11. The apparatus of claim 9 wherein the matrix medium is between 1 mm and 20 mm thick, preferably between 2 and 10 mm thick.

12. The apparatus of claim 11 wherein the means for successively generating an attenuation signal is a light detector system, said detector system in general alignment with the laser source along a line perpendicular to the laser's collimated beam, said detector system positioned on a side opposite of that which is transpierced by the laser's collimated beam, and generating attenuation signals proportional to the total attenuation of beams passing through said matrix at a plurality of locations defining said matrix.

13. The apparatus of claim 12 wherein the means for reconstructing all weighted values in response to said beam attenuation signals is a digital computer comprising:
   (a) a means to convert said attenuation signals into digital signals;
   (b) a means to store said digital signals;
   (c) a means responsive to said stored digital signals for converting digital signals into corresponding analog signals proportional to said derived weighted values.

14. The apparatus of claim 13 wherein the means for displaying each reconstructed value is a cathode ray tube means, responsive to said analog signals, for generating a pictorial representation of all matrix locations transpierced by said beam with a proportional intensity.

15. The apparatus of claim 1 wherein permeability changes over time are determined, further comprising:
   a sealed container having a fluid inlet and fluid outlet, said container housing a matrix section; and
   a first fluid, and a second fluid to displace the first fluid within the container, said second fluid reacting with clays present in said matrix section to cause a change in permeability.

16. The apparatus of claim 1 wherein grain size and grain size variation of the matrix medium are measured, and where said means for generating an attenuation signal is a light detection system comprising a plurality of small light detectors in a fixed array.

17. The apparatus of claim 16 wherein the light detectors have an area preferably 2 mm×2 mm.

18. A method modeling fluid flow within a matrix medium comprising the steps of:
   constructing a sealed representation of all zones of differing permeability within a matrix medium;
   interposing a light enhancing pore-filling fluid to symbiotically interact with said matrix medium;
   flooding said matrix medium with an isotropic light source;
   measuring the attenuation of said isotropic light at a plurality of locations within said matrix, said attenuation being correlatable to steady state fluid flow.

19. The method of claim 18 wherein dynamic flow patterns are modeled further comprising the steps of:
   injecting a second fluid into said matrix to drive the initial pore-filling fluid;
   measuring both the change in attenuation of said isotropic light at the interface of said second fluid and said measuring means, and the time of arrival of said second fluid interface at said measuring means;
   generating a prediction of fluid flow based on measured attenuation as a function of the light source and attenuation measuring means properties reflection coefficients at the fluid interface, and the photon means free path in each zone.

* * * * *